(12) United States Patent
Raizada et al.

(10) Patent No.: US 9,279,139 B2
(45) Date of Patent: Mar. 8, 2016

(54) MEDIA COMPRISING A GLUTAMINE BIOSENSOR AND METHODS OF USE THEREOF

(75) Inventors: Manish Raizada, Guelph (CA); Michael Tessaro, Caledonia (CA); Hanan Reda Hassan Elsayed Shehata, Guelph (CA)

(73) Assignee: University of Guelph, Guelph, Ontario (CA)

( * ) Notice: Subject to any disclaimer, the term of this patent is extended or adjusted under 35 U.S.C. 154(b) by 0 days.

(21) Appl. No.: 14/127,863

(22) PCT Filed: Jun. 20, 2012

(86) PCT No.: PCT/CA2012/000601
§ 371 (c)(1),
(2), (4) Date: Mar. 13, 2014

(87) PCT Pub. No.: WO2012/174646
PCT Pub. Date: Dec. 27, 2012

(65) Prior Publication Data
US 2014/0329271 A1  Nov. 6, 2014

Related U.S. Application Data

(60) Provisional application No. 61/499,286, filed on Jun. 21, 2011.

(51) Int. Cl.
*G01N 33/68* (2006.01)
*C12Q 1/02* (2006.01)
*C12Q 1/04* (2006.01)

(52) U.S. Cl.
CPC .. *C12Q 1/02* (2013.01); *C12Q 1/04* (2013.01); *C12Q 1/045* (2013.01); *G01N 33/6812* (2013.01)

(58) Field of Classification Search
USPC .......................................... 435/34, 29, 4, 419
See application file for complete search history.

(56) References Cited

U.S. PATENT DOCUMENTS

| | | | | |
|---|---|---|---|---|
| 4,780,191 | A * | 10/1988 | Romette et al. | 204/403.1 |
| 5,411,866 | A * | 5/1995 | Luong et al. | 435/14 |
| 2001/0031492 | A1 * | 10/2001 | Lewington et al. | 435/252.1 |
| 2003/0108980 | A1 * | 6/2003 | Sayler et al. | 435/34 |
| 2008/0261255 | A1 * | 10/2008 | Tolosa et al. | 435/15 |
| 2011/0201100 | A1 * | 8/2011 | Proulx et al. | 435/288.7 |

OTHER PUBLICATIONS

International Search Report and Written Opinion in International Application No. PCT/CA2012/000601, mailed Sep. 27, 2012, 12 pages.
Allan and Shelp, "Fluctuations of gamma aminobutyrate, gammahydroxybutyrate, and related amino acids in Arabidopsis leaves as a function of the light-dark cycle, leaf age, and N stress," *Canadian Journal of Botany*, 84: 1339-1346, 2006.
Baba et al., "Construction of *Escherichia coli* K-12 in-frame, single-gene knockout mutants: the Keio collection," *Molecular Systems Biology*, 2, 11 pages, 2006.
Bauer et al., "Amino acid metabolism of pea leaves—labeling studies on utilization of amides," *Plant Physiology*, 59:920-924, 1977.
Becana et al., "Structure and function of leg hemoglobins," *An. Estac. Exp. Aula Dei (Zaragoza)*, 21(3): 203-208, 1995.
Bertels et al., "Design and characterization of auxotropy-based amino acid biosensors," *PLoS ONE*, 7(7):e41349, Jul. 2012.
Boddey et al., "Biological nitrogen fixation associated with sugarcane and rice: Contributions and prospects for improvement," *Plant and Soil*, 174( 1): 195-209, 1995.
Bredemeier and Schmidhalter, Laser-induced chlorophyll fluorescence to determine the nitrogen status of plants, *Plant Nutrition*, 92:726-727, 2001.
Casagrande et al., "Factors limiting the grain protein content of organic winter wheat in south-eastern France: a mixed-model approach," *Agronomy for Sustainable Development*, 29:565-574, 2009.
Catalano et al., "Biochemical characterization of symbiosome membrane proteins from Medicago truncatula root nodules," *Electrophoresis*, 25(3): 519-531, 2004.
Chalova et al., "Application of an *Escherichia coli* green fluorescent protein-based lysine biosensor under nonsterile conditions and autofluorescence background," *Letters in Applied Microbiology*, 42:265-270, 2006.
Chalova et al., "Quantification of total and bioavailable lysine in feed protein sources by a whole-cell green fluorescent protein growth based *Escherichia coli* biosensor," *Applied Microbiology and Biotechnology*, 76:91-99, 2007.
Chapman and Leech, "Changes in Pool sizes of free amino acids and amides in leaves and plastids of *Zea mays* during leaf development," *Plant Physiology*, 63:567-572, 1979.
Chapman and Miller, "Nitrate transporters and root architecture," *Transporters and Pumps in Plant Signaling*, 165-190, 2011.
Chinnusamy et al., "Screening for gene regulation mutants by bioluminescence imaging," *Science STKE*, 10 pages, Jul. 2002.
Christenson, " Detection systems optimized for low-light chemiluminescence imaging," *Luminescence Biotechnology: Instruments and Applications*, 469-481, 2002.
Crawford and Glass, "Molecular and physiological aspects of nitrate uptake in plants," *Trends in Plant Science*, 3:389-395, Oct. 1998.
Crawford, "Nitrate—nutrient and signal for plant-growth," *Plant Cell*, 7:859-868, Jul. 1995.
Crochet et al., "Site-selective dual modification of periplasmic binding proteins for sensing applications," *Biosensors & Bioelectronics*, 26:55-61, May 2010.

(Continued)

*Primary Examiner* — Ralph Gitomer
(74) *Attorney, Agent, or Firm* — Fish & Richardson P.C.

(57) ABSTRACT

An essentially glutamine-free medium comprising a whole-cell glutamine biosensor, comprising a glutamine auxotrophic *E. coli* and a Lux reporter gene, for detecting glutamine in an analyte. The medium is useful in methods to detecting, screening, identifying and selecting nitrogen-fixing microbes and in methods of determining the nitrogen state of plants, plant products and soil.

9 Claims, 15 Drawing Sheets

(56) References Cited

OTHER PUBLICATIONS

Danso, "Assessment of biological nitrogen fixation," *Nutrient Cycling in Agroecosystems*, 42( 1):33-41, 1995.

Dattelbaum et al., "Optimal determination of glutamine using a genetically engineered protein," *Analytical Biochemistry*, 291:89-95, 2001.

Desouky et al., "Detection of nitrate/nitrite bioavailability in wastewater using a lux CDABE-based *Klebsiella oxytoca* bioluminescent bioreporter," *J. Microbiol. Biotechnol.*, 17(8):1254-1261, 2007.

Dixon and Kahn, "Genetic regulation of biological nitrogen fixation," *Nat Rev Micro*, 2(8): 621-631, Aug. 2004.

Eckstein et al., "Analysis of glutamine, glutamate, pyroglutamate, and GABA in cerebrospinal fluid using ion pairing HPLC with positive electrospray LC/MS/MS," *Journal of Neuroscience Methods*, 171: 190-196, Feb. 2008.

Erickson et al., "A bioluminescent *Escherichia coli* auxotroph for use in an in vitro lysine availability assay," Journal of Microbiological Methods, 40:207-212, 2000.

Fischer et al., "Amino acid transport in plants," Trends in Plant Science, 3:188-195, May 1998.

Fonteh et al., "Quantification of free amino acids and dipeptides using isotope dilution liquid chromatography and electrospray ionization tandem mass spectrometry," *Amino Acids*, 32:203-212, 2007.

Foyer et al., "Markers and signals associated with nitrogen assimilation in higher plants.," *Journal of Experimental Botany*, 54:585-593, Jan. 2003.

Fuentes et al., "Over-expression of cytosolic glutamine synthetase increases photosynthesis and growth at low nitrogen concentrations," *Journal of Experimental Botany*, 52: 1071-1081, May 2001.

Gholizadeh et al., "Evaluation of leaf total nitrogen content for nitrogen management in a Malaysian paddy field by using soil plant analysis development chlorophyll meter," *American Journal of Agricultural and Biological Sciences*, 4:278-282, 2009.

Gill and Eisenberg, "The crystal structure of phosphinothricin in the active site of glutamine synthetase illuminates the mechanism of enzymatic inhibition," *Biochemistry*, 40:1903-1912, Jan. 2001.

Gillor et al., A *Synechococcus* PglnA::luxAB fusion of estimation of nitrogen bioavailability to freshwater cyanobacteria, *Appl. Environ. Microbiol.*, 69(3):1465-1474, Mar. 2003.

Glass et al., "The regulation of nitrate and ammonium transport systems in plants," *Journal of Experimental Botany*, 53:855-864, Apr. 2002.

Hitchins et al., "The use of *Escherichia coli* mutants to measure the bioavailability of essential amino acids in foods," *Plant Foods for Human Nutrition*, 39: 109-120, 1989.

Hong et al., "Rapid determination of L-glutamine using engineered *Escherichia coli* overexpressing glutamine synthetase," *Appl. Biochem. Biotechnol.*, 158:398-407, 2009.

Jaeger et al., "Mapping of sugar and amino acid availability in soil around roots with bacterial sensors of sucrose and tryptophan," *Applied and Environmental Microbiology*, 65:2685-2690, Jun. 1999.

Kahindi et al. "Biological nitrogen fixation," *Encyclopedia of Life Support Systems: Biotechnology*, 15:104-111, 2001.

Kirkman and Miflin, "Nitrate content and amino acid composition of the xylem fluid of spring wheat throughout the growing season," *Journal of the Science of Food and Agriculture*, 30:653-660, 1979.

Lee et al., "Nitrogen assimilation and the control of ammonium and nitrate absorption by maize roots," *Journal of Experimental Botany*, 43: 1385-1396, Nov. 1992.

Li et al., "The developmental dynamics of the maize leaf transcriptome," *Nature Genetics*, 42(12):1060-1069, Dec. 2010.

Lohaus et al., "Transport of amino acids with special emphasis on the synthesis and transport of asparagine in the Illinois low protein and Illinois high protein strains of maize," *Planta*, 205: 181-188, 1998.

Looger et al., "Computational design of receptor and sensor proteins with novel functions," *Nature*, 423: 185-190, May 2003.

Loper and Lindow, A biological sensor for iron available to bacteria in their habitats on plant surfaces, *Applied and Environmental Microbiology*, 60: 1934-1941, Jun. 1994.

Magalhaes et al., "Kinetics of $^{15}NH_4^+$ assimilation in *Zea mays*—preliminary studies with a glutamate dehydrogenase (GDH1) null mutant," *Plant Physiology*, 94:647-656, Jun. 1990.

Majeran et al., "Structural and metabolic transitions of C4 leaf development and differentiation defined by microscopy and quantitative proteomics in maize," *The Plant Cell*, 22: 3509-3042, Nov. 2010.

Mayer et al., "The Isolation and characterization of glutamine-requiring strains of *Escherichia-coli*-K12," *Molecular & General Genetics*, 137:131-142, 1975.

Meighen and Szittner, "Multiple repetitive elements and organization of the lux operons of luminescent terrestrial bacteria," *Journal of Bacteriology*, 174:5371-5381, Aug. 1992.

Micallef et al., "Quantification of $^{14}C$-Labeled amino-acids by reverse-phase high-performance liquid-chromatography," *Journal of Liquid Chromatography*, 12(7):1281-1300, 1989.

Miflin and Habash, "The role of glutamine synthetase and glutamate dehydrogenase in nitrogen assimilation and possibilities for improvement in the nitrogen utilization of crops," *Journal of Experimental Botany*, 53:979-987, Apr. 2002.

Miller and Smith, "Nitrate transport and compartmentation in cereal root cells," *Journal of Experimental Botany*, 47:843-854, Jul. 1996.

Miller et al., "Amino acids and nitrate as signals for the regulation of nitrogen acquisition," *Journal of Experimental Botany*, 59: 111-119, Dec. 2007.

Molnar-Perl, "Quantitation of amino acids and amines in the same matrix by high performance liquid chromatography, either simultaneously or separately," *Journal of Chromatography*, 987:291-309, 2003.

Montemurro et al., "Nitrogen application in winter wheat grown in Mediterranean conditions: effects on nitrogen uptake, utilization efficiency, and soil nitrogen deficit," *Journal of Plant Nutrition*, 30: 1681-1703, 2007.

Niu et al., "Transpiration, and nitrogen uptake and flow in two maize(*Zea mays* L.) inbred lines as affected by nitrogen supply," *Annals of Botany*, 99:153-160, 2007.

Ohlson et al., "Accumulation of amino acids in forest plants in relation to ecological amplitude and nitrogen supply," *Functional Ecology*, 9:596-605, Aug. 1995.

Oliveira and Coruzzi, "Carbon and amino acids reciprocally modulate the expression of glutamine synthetase in Arabidopsis," Plant Physiol., 121:301-310, Sep. 1999.

Ott et al., "Symbiotic leghemoglobins are crucial for nitrogen fixation in legume root nodules but not for general plant growth and development," *Current Biology*, 15(6): 531-535, Mar. 2005.

Paau, "Improvement of Rhizobium inoculants by mutation, genetic engineering and formulation," *Biotechnology Advances*, 9(2): 173-184, 1991.

Payne et al., "Use of an *Escherichia coli* Lys-auxotroph to assay nutritionally available lysine in biological materials," Journal of Applied Bacteriology, 42:165-177, 1977.

Peoples and Gifford, "Long-distance transport of carbon and nitrogen from sources to sinks in higher plants," *Plant Physiology, Biochemistry and Molecular Biology*, 442-447, 1990.

Pfleger et al., "Microbial sensors for small molecules: development of a mevalonate biosensor," *Metabolic Engineering*, 9:30-38, 2007.

Rogers, "Principles of affinity-based biosensors," *Molecular Biotechnology*, 14:109-129, 2000.

Rozan et al., "Free amino acids present in commercially available seedlings sold for human consumption: a potential hazard for consumers," *Journal of Agricultural and Food Chemistry*, 48:716-723, Feb. 2000.

Rubio-Covarrubias et al., "Evaluating foliar nitrogen compounds as indicators of nitrogen status in Prunus persica trees," *Scientia Horticulturae*, 120:27-33, 2009.

Shelp and Dasilva, "Distribution and metabolism of xylem-borne ureido and amino compounds in developing soybean shoots," *Plant Physiology*, 94: 1505-1511, 1990.

Smil, "Nitrogen and food production: protein for human diets," *Ambio*, 31 :126-131, Mar. 2002.

Soudry et al., "Accumulation and remobilization of amino acids during senescence of detached and attached leaves; in planta Analysis

(56) References Cited

OTHER PUBLICATIONS of tryptophan levels by recomginant luminescent bacteria," *J. Expert. Botany*, 56(412):695-702, Feb. 2005.

Hill, "How is nitrogenase regulated by oxygen?" *FEMS Microbiology Letters*, 54(2):111-129, 1988.

Tecon and Van Der Meer, "Bacterial biosensors for measuring availability of environmental pollutants," *Sensors*, 8:4062-4080, Jul. 2008.

Tejera et al., "Nitrogen compounds in the apoplastic sap of sugarcane stem: some implications in the association with endophytes," *Journal of Plant Physiology*, 163:80-85, 2006.

Tessaro et al., "Bacterial whole-cell biosensor for glutamine with applications for quantifying and visualizing glutamine in plants," *Appl. Environ. Microbiol.*, 78(2):604-606, 2012.

Tessaro et al., "Glutamine biosensor as a new tool for plant physiology," CSPP-SCPV Eastern Regional Meeting & PDW, University of Guelph, p. 32, 2009.

Thiele et al., "Analysis of amino acids without derivatization in barley extracts by LC-MS-MS," *Analytical and Bioanalytical Chemistry*, 391:2663-2672, 2008.

Tuffnell and Payne, "A colorimetric enzyme assay using *Escherichia coli* to determine nutritionally available lysine in biological materials," *Journal of Applied Bacteriology*, 58:333-341, 1985.

Unkovich et al., "Measuring plant-associated nitrogen fixation in agricultural systems," *Australian Centre for International Agricultural Research*, 260 pages, 2008.

Vidmar et al., "Regulation of high-affinity nitrate transporter genes and high-affinity nitrate influx by nitrogen pools in roots of barley," *Plant Physiol.*, 123:307-318, May 2000.

Wang et al., "Effects of fertilization and other agronomic measures on nutritional quality of crops," *Journal of the Science of Food and Agriculture*, 88:7-23, 2008.

White et al., "Nutrient sharing between symbionts," *Plant Physiology*, 144(2): 604-614, Jun. 2007.

Wolde-Meskel et al. "Genetic diversity and phylogeny of rhizobia isolated from agroforestry legume species in southern Ethiopia," *International Journal of Systematic and Evolutionary Microbiology*, 55: 1439-1452, 2005.

Yang et al., "H+-independent glutamine transport in plant root tips," *PLoS One*, 5:e8917, Jan. 2010.

\* cited by examiner

MEDIA COMPRISING A GLUTAMINE BIOSENSOR AND METHODS OF USE THEREOF

CROSS-REFERENCE TO RELATED APPLICATIONS

This application is a National Stage Application under 35 U.S.C. §371, and claims the benefit of International Application No. PCT/CA2012/000601, filed Jun. 20, 2012, which claims benefit of priority from U.S. Provisional Application No. 61/499,286, filed Jun. 21, 2011. The disclosures of the foregoing applications are hereby incorporated by reference in their entirety.

FIELD OF THE INVENTION

The present invention is directed to nitrogen fixation and, more specifically, to a medium for detecting glutamine and methods and uses thereof.

BACKGROUND OF THE INVENTION

Nitrogen is one of the pillars of worldwide agricultural production. Many have argued that improving the efficiency with which fertilizer nitrogen is used in world agriculture is essential to the long-term sustainability of the planet.

The amino acid glutamine (Gln) is a critical intermediate in nitrogen metabolism across all life. In plants, nitrogen fertilizer is assimilated into Gln (12, 39) and subsequently glutamate; together, these amino acids serve as nitrogen donors for various reactions, including the biosynthesis of other amino acids (34, 39). These amino acids further regulate uptake and assimilation of soil nitrate and ammonium (13, 25, 29, 40, 61). Gln, as well as asparagine, are important forms of nitrogen used for long-distance transport in the plant, including from root to shoot (49). In fact, the application of nitrogen fertilizer to the roots of maize (Zea mays L.) plants can generate a large increase in the levels of Gln and other amino acids within 30-120 min in the root and shoot, respectively (34). Gln is thus a key indicator of nitrogen status in plants. Unfortunately, only indirect or delayed assays currently exist to quantify plant nitrogen status, in spite of the importance of nitrogen as the most limiting soil nutrient in global agriculture (55).

Free Gln is primarily quantified using high performance liquid chromatography (HPLC)-based analysis of tissue extracts (1, 38, 43, 47). There has been limited use of biosensors for Gln quantification. The Gln-binding protein (QBP) (32), originating from the periplasmic space of bacteria, has been used to construct reagentless sensors for Gln for use with aqueous extracts (14, 15). For cell biology applications, a Förster resonance energy transfer (FRET) QBP-based biosensor has been engineered in transgenic Arabidopsis plants to monitor Gln uptake by root tips under a fluorescent microscope (63). This biosensor achieves millimolar sensitivity with superb sub-cellular resolution and good specificity for Gln, but requires the creation of transgenic plants which may be less suited for high throughput applications, including determination of plant nitrogen status.

Microbial whole cell biosensors have been used as inexpensive tools to quantify analytes from biological extracts into which they are co-inoculated (18, 50). They have also been used to visualize analytes in intact tissues of non-transgenic organisms. For example, the leakage of sucrose, tryptophan or iron can be sensed in plants using nearby microbial biosensor cells and then imaged (27, 33).

A subset of microbial biosensors have been based on auxotrophs expressing a constitutive reporter (e.g. green fluorescent protein, GFP, lux). An auxotroph is an organism that cannot grow in the absence of a particular metabolite. The use of amino acid auxotrophs for the quantification of bioavailable essential amino acids such as lysine in human and animal foodstuffs originated decades ago (6, 7, 18, 26, 48, 60). A Gln auxotroph of *Escherichia coli* has been generated by down-regulation of the gene encoding glutamine synthetase (GlnA) (36).

Most of the currently available methods for glutamine measurement have the disadvantages of being expensive, time consuming and requiring some level of technical expertise. Furthermore, conventional methods are indirect or delayed. It is therefore desirable to provide compositions, media, and methods for detecting glutamine that mitigate at least one of the problems or disadvantages of the prior art.

SUMMARY OF THE INVENTION

The present invention provides a medium for detecting glutamine in a wide variety of samples such as, but not limited to, plants or plant products, soil, and in microbes. Because the presence of glutamine in plants, soils, or microbes can be used as an indicator of nitrogen levels, the medium may be used in methods to identify, screen for, select, or detect nitrogen-fixation, or nitrogen content in plants, plant products, or soil, or to identify, screen for, select, detect, or culture nitrogen-fixing microbes or inoculant nitrogen-fixing microbes.

In aspects, the medium comprises a glutamine biosensor to indicate the nitrogen or, more specifically, the glutamine status of a microbe, plant, or soil. The glutamine biosensor provides a signal whenever glutamine is present in a sample or analyte added to the medium. The signal may be qualitative, in that it provides information about whether or not there is nitrogen or glutamine in the analyte. The signal may also be quantitative, in that it provides a measurement of the amount of nitrogen or glutamine in the analyte. The medium is essentially free of glutamine, meaning that little to no glutamine is present in the medium.

According to an aspect of the present invention, there is provided an essentially glutamine-free growth medium comprising a glutamine biosensor for detecting glutamine in an analyte.

According to an aspect of the present invention, the glutamine biosensor comprises a bacterial cell, such as *E. coli*. In another aspect, the bacterial cell is a glutamine auxotroph. In another aspect, glutamine synthetase is down-regulated in the bacterial cell as compared to a wild-type bacterial cell.

According to another aspect of the present invention, the bacterial cell comprises a reporter gene that is expressed in the presence of glutamine. In another aspect, the reporter gene is lux.

In an aspect of the present invention, the glutamine biosensor is the *E. coli* strain GlnLux.

In another aspect of the present invention, the growth medium is Lysogeny Broth (LB), M9 medium, agar, or combinations thereof.

In an aspect of the present invention, the medium further comprises casamino acids, which may be present in an amount of about 0.5% v/v. The medium may further comprises a protease inhibitor or a cocktail of protease inhibitors, which may be present in an amount of about 1% v/v.

In another aspect of the present invention, the medium is liquid, solid, or semi-solid.

In another aspect of the present invention, the glutamine biosensor is diluted up to about 1000-fold.

According to another aspect of the present invention, there is provided a use of the medium described herein for culturing, screening, detecting, or selecting a nitrogen-fixing microbe or an inoculant nitrogen-fixing microbe.

According to another aspect of the present invention, there is provided a use of the medium described herein for identifying, screening for, detecting, or quantifying glutamine content in an analyte.

In an aspect of the present invention, the analyte is a plant, plant organ, seed, soil, or an extract thereof. In another aspect, the plant, plant organ, or seed is a legume or a cereal or the extract is derived from a legume or a cereal. In an aspect, the cereal is maize. In another aspect, the plant, plant organ or seed is a green manure or the extract is derived from a green manure. In another aspect, the analyte is a microbe, such as a bacterium or a fungus. In an aspect, the bacterium is *Rhizobium*. In another aspect, the microbe is an endophyte, such as a maize endophyte.

According to another aspect of the present invention, there is provided a method for identifying, screening for, detecting or selecting a nitrogen-fixing microbe or an inoculant nitrogen-fixing microbe, the method comprising the steps of 1) culturing the microbe in the medium described herein; and 2) visualizing and/or measuring a signal from the glutamine biosensor to identify, screen for, detect or select the microbe.

In an aspect, the method is for selecting for nitrogen-fixing microbes or inoculant nitrogen-fixing microbes in a high-throughput assay.

According to another aspect of the present invention, there is provided a method for identifying, screening for, detecting or selecting a nitrogen-fixing microbe or an inoculant nitrogen-fixing microbe, the method comprising the steps of 1) culturing the microbe in the medium described herein; and 2) quantifying a signal from the glutamine biosensor to identify, screen for, detect or select the microbe.

According to another aspect of the present invention, there is provided a method for identifying, screening for, or detecting nitrogen fixation in a plant, plant organ, seed, soil, or extract thereof, the method comprising the steps of 1) placing at least a portion of the plant, plant organ, seed, soil, or extract thereof on or in the medium described herein and 2) visualizing and/or quantifying a signal from the glutamine biosensor as indicative of nitrogen fixation.

In an aspect, the method is for detecting nitrogen fixation in a plant, plant organ, seed, soil, or extract thereof so as to determine the effects of different environmental conditions and/or plant genotypes on nitrogen fixation in the plant, plant organ, seed, soil, or extract thereof.

In an aspect of the present invention, about 1 mg of the plant, plant organ, seed, soil, or extract thereof is placed on or in the medium. In another aspect, the plant, plant organ, seed, soil, or extract thereof is diluted up to about 1000-fold prior to placing on or in the medium.

In yet another aspect of the present invention, the medium is solid and the plant, plant organ, seed, soil, or extract thereof is placed on the medium. In another aspect, the medium is solid and the plant, plant organ, seed, soil, or extract thereof is embedded within the medium.

In another aspect, the at least a portion of the plant, plant organ, seed, soil, or extract thereof is a leaf punch.

According to another aspect of the present invention, there is provided a method for quantifying nitrogen content in a plant, plant extract, plant organ, seed or soil, the method comprising the steps of 1) placing the plant, plant organ, seed or soil on the medium described herein; and 2) measuring a signal from the glutamine biosensor to thereby quantify the nitrogen content of the plant, plant extract, plant organ, seed or soil.

According to another aspect of the present invention, there is provided a glutamine biosensor, the glutamine biosensor comprising an essentially glutamine-free culture of the Gln-Lux strain of *E. coli* cells.

According to another aspect of the present invention, there is provided a method for determining whether soil requires fertilization to support the growth of a plant, the method comprising the steps of 1) placing format least a portion of the plant in or on the medium described herein; and 2) visualizing and/or measuring a signal from the glutamine biosensor, wherein an absent signal or a signal below a predetermined level indicates that the soil requires fertilization.

According to another aspect of the present invention, there is provided a method for determining whether a microbe is a nitrogen-fixing microbe, the method comprising the steps of 1) placing a culture of the microbe in or on the medium described herein; and 2) visualizing or measuring a signal from the glutamine biosensor; wherein the presence of a signal indicates that the microbe is a nitrogen-fixing microbe.

In an aspect of the present invention, the microbe is a bacterium or fungus. In an aspect, the bacterium is *Rhizobium*. In another aspect, the microbe is an endophyte, such as a maize endophyte.

In accordance with another aspect of the present invention, there is provided a method for identifying, screening for, detecting, or quantifying glutamine content in an analyte, the method comprising the steps of 1) placing the analyte on or in the medium described herein; and 2) visualizing and/or measuring a signal from the glutamine biosensor as indicative of glutamine content in the analyte.

In an aspect, the analyte is a plant, plant organ, seed, soil, or an extract thereof. In another aspect, the plant, plant organ, or seed is a legume or a cereal or the extract is derived from a legume or a cereal, such as maize. In another aspect, the plant, plant organ, or seed is a green manure or the extract is derived from a green manure.

In another aspect, the analyte is a microbe or an extract thereof. In an aspect, the microbe is a bacterium or a fungus or the extract is derived from a bacterium or fungus, such as *Rhizobium*. In another aspect, the microbe is a bacterial endophyte, such as a maize endophyte.

In accordance with another aspect of the present invention, there is provided a method for predicting plant efficiency in absorbing and assimilating soil nitrogen and/or in scavenging nitrogen from senescing plant cells, the method comprising the steps of 1) placing at least a portion of the plant or an extract thereof in or on the medium described herein; and 2) visualizing and/or measuring a signal from the glutamine biosensor, wherein the presence of a signal indicates predicted efficiency in absorbing and assimilating soil nitrogen and/or scavenging nitrogen from senescing plant cells.

In an aspect, the presence of a signal at or above a predetermined level indicates predicted efficiency in absorbing and assimilating soil nitrogen and/or scavenging nitrogen from senescing plant cells. In another aspect, intensity of the signal is positively correlated with predicted efficiency in absorbing and assimilating soil nitrogen and/or scavenging nitrogen from senescing plant cells.

In accordance with another aspect, the signal is visualized and/or measured using a CCD camera or a luminometer.

In accordance with another aspect, there is provided an assay for biological nitrogen fixation, the assay comprising the medium described herein.

In an aspect, the assay further comprises a CCD camera or a luminometer for detecting a signal from the medium in the presence of an analyte that exhibits nitrogen fixation.

In another aspect, the assay further comprises instructions for use.

In another aspect, the assay further comprises a mail-in package for shipping the assay to a secondary location for determining the result of the assay.

The present invention presents many advantages in that it is simple, inexpensive and easy to use. Downstream advantages of aspects of the present invention on agricultural systems include the discovery and improvement of strains of microbial inoculants, more efficient crop production, better management of nitrogen fertilizers and soil amendments and the reduction of the dependence on nitrogen fertilizers.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from the detailed description.

BRIEF DESCRIPTION OF THE DRAWINGS

Embodiments of the present invention will now be described more fully with reference to the accompanying drawings:

In FIG. 3A, an initial determination of the linear concentration range of Gln using the GlnLux assay (1/10 $OD_{595}$ 0.025) is shown. In FIGS. 3B to 3I, statistical measurements of linearity for the following incubation times are plotted: (FIG. 3B,3C) 2 h, (FIG. 3D,3E) 3 h, (FIG. 3F,3G) 4 h, and (FIG. 3H,3I) 5 h. Linearity of the GlnLux response was quantified using Goodness of Fit ($R^2$) and measured along with the mean slope (m).

FIG. 4A to 4C show the measurements of the specificity of GlnLux cells for Gln. GlnLux cells (1/10 $OD_{595}$ 0.025) were incubated for 3 h with Gln standards (Phase 3) along with dilutions of: (FIG. 4A) nitrite ($NO_2^-$), (FIG. 4B) nitrate ($NO_3^-$) or (FIG. 4C) an amino acid cocktail of 19 amino acids (AA).

FIGS. 6A and 6B show the effect of depleting endogenous Gln in M9-agar; FIG. 6C to 6E show the effect of GlnLux culture density (v/v using $OD_{595}$=1.0); FIG. 6F to 6I show the effect of supplementing M9-agar with casamino acids (w/v); FIG. 6J to 6L show the effect of altering the incubation duration of the GlnLux in agar with Gln-containing filter paper, prior to imaging.

FIG. 7A to 7H shows the result of maize seedlings treated either with nitrogen fertilizer or none, harvested plant organs were freeze-thawed to cause Gln leakage, and then were placed on GlnLux in agar; the opposite agar surface was then imaged using a photon capture CCD camera. Shown are representative pictures of: (FIG. 7A) a root system not previously exposed to nitrate; (FIG. 7B) a root system previously exposed to nitrate; (FIG. 7C to 7E) leaves from unfertilized plants; (FIG. 7F to 7H) leaves from ammonium/nitrate-fertilized plants; (FIG. 7I) leaf number 2 from different nitrate-fertilized plants showing consistent spatial distribution of Gln. For FIGS. 7C-7H, the leaf tip numbers from left to right were 1, 2 and 4. Shown are the light images (FIG. 7C, 7F), white lux images (FIG. 7D, 7G), and false-coloured lux images (FIG. 7A, 7B, 7E, 7H, 7I).

FIG. 9A to 9T show the effect of diluting GlnLux cultures on the incubation time required to achieve a linear response in the luminometer assay. GlnLux cell cultures were diluted as indicated ($1/10^{th}$ or $1/100^{th}$ dilutions of $OD_{595}$=0.025) in Phase 2 prior to depletion of endogenous Gln and then incubated for the following durations with free Gln standards: (FIG. 9A-9D) 3 h, (FIG. 9E-9H) 5 h, (FIG. 9I-9L) 7 h, (FIG.

9M-9P) 9 h, (FIG. 9Q-9T) 12 h. The linearity of the GlnLux response was quantified using Goodness of Fit ($R^2$) and measured along with the mean slope (m). The most linear response is boxed or circled at the low and high concentration ranges of Gln, respectively.

Figure 10:
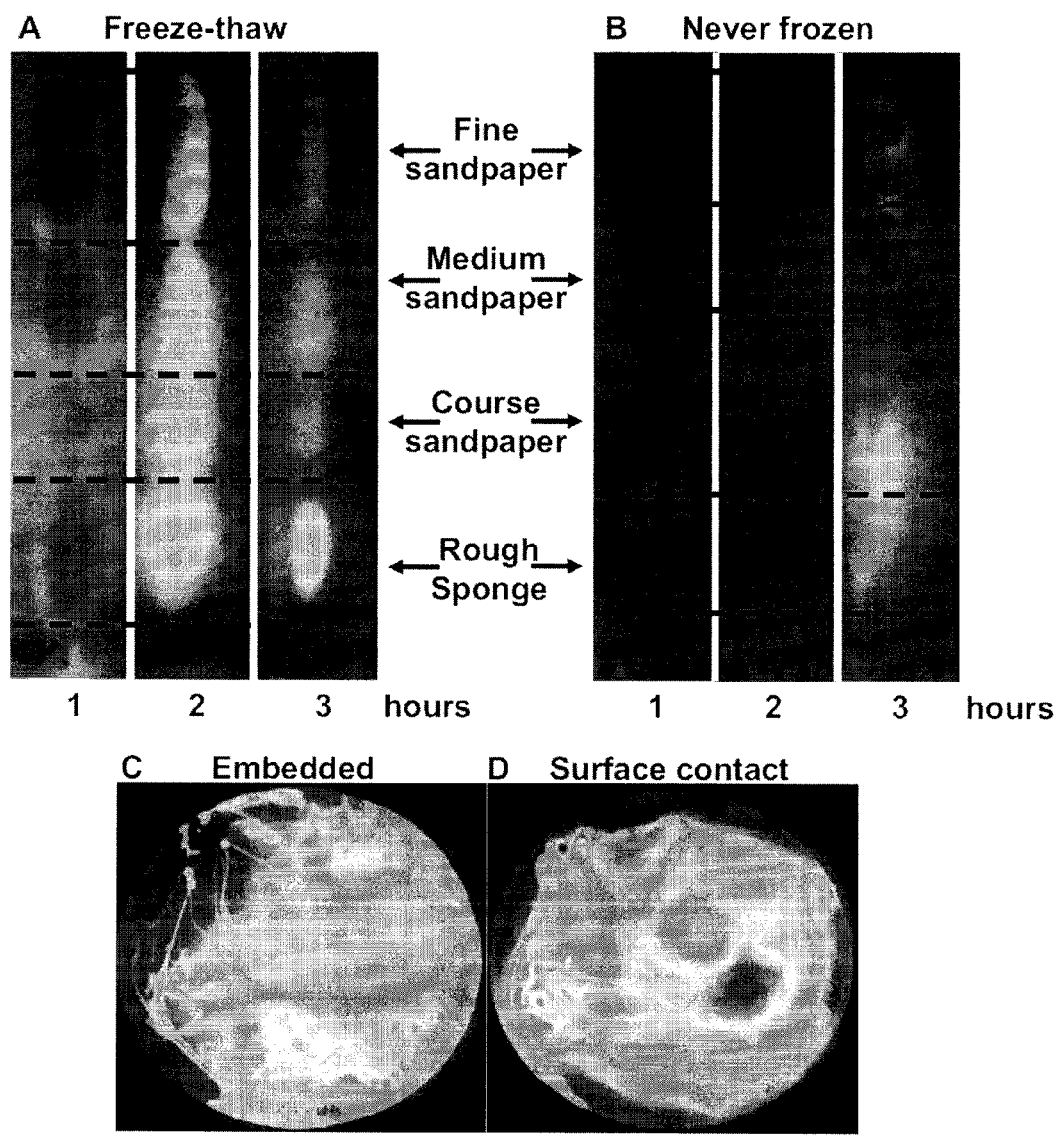

FIG. 10A to 10D show the improvement of plant tissue treatments to enable visual screening of Gln in planta using a photon capture camera. Shown are the effects of (FIG. 10A) freeze-thawing a maize leaf immediately before application onto GlnLux in agar, versus (FIG. 10B) the room temperature control, combined with abrasive treatments using different grades of sandpaper or the rough side of a sponge. (FIG. 10C, 10D) show a comparison of the response of GlnLux-agar when plant root tissues were embedded in the agar (FIG. 10C), versus being laid on the GlnLux in agar surface (FIG. 10D). Shown are 600 s exposures.

FIGS. 11A, 11B and 11C show a first (FIG. 11A), second (FIG. 11B) and third (FIG. 11C) attempt in imaging *Bradyrhizobium japonicum* wild-type nitrogen fixing strain 110 (nif+), and mutant strain 510 (nif−) which is deficient in fixing nitrogen, in GlnLux-agar. *B. japonicum* colonies were incubated on Gln-Lux-agar for 8-22 h. Photon capture CCD images shown used 10 minute exposure times.

FIG. 12A to F show the engineering and initial testing of the glutamine biosensor for soil nitrogen availability to help corn farmers decide whether or not to "top up" (sidedress) nitrogen fertilizer in the initial weeks after sowing. Shown is detection of differences in soil nitrogen availability using the GlnLux biosensor applied to leaf punches (1 cm diameter) from two-week old corn seedlings growing in the field. The biosensor test could distinguish 35 lbs/acre nitrogen (FIG. 12A) from 80 lbs/acre nitrogen (FIG. 12B) and from ≥130 lbs/acre N (FIGS. 12C, 12D, 12E, and 12F).

Figure 13:
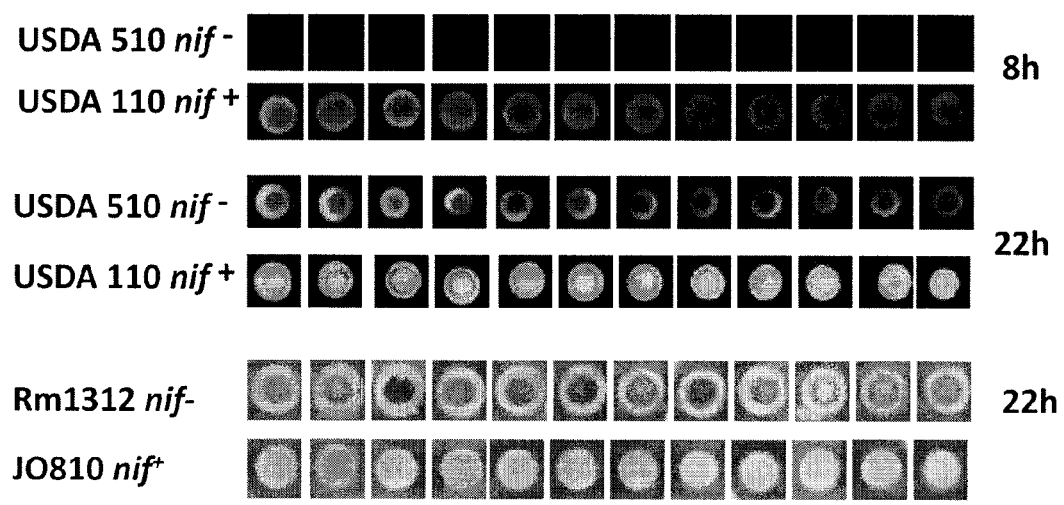

FIG. 13 shows the validation of the glutamine biosensor technology for ability to detect microbial biological nitrogen fixation (BNF). Colonies of *Bradyrhizobium japonicum* (510, 110) and *Sinorhizobium meliloti* (1312, J0810) wild type versus mutant nif− strains on GlnLux agar after incubation for 8-22 hrs. Images were taken using CCD camera using a 600 sec exposure.

Figure 14:
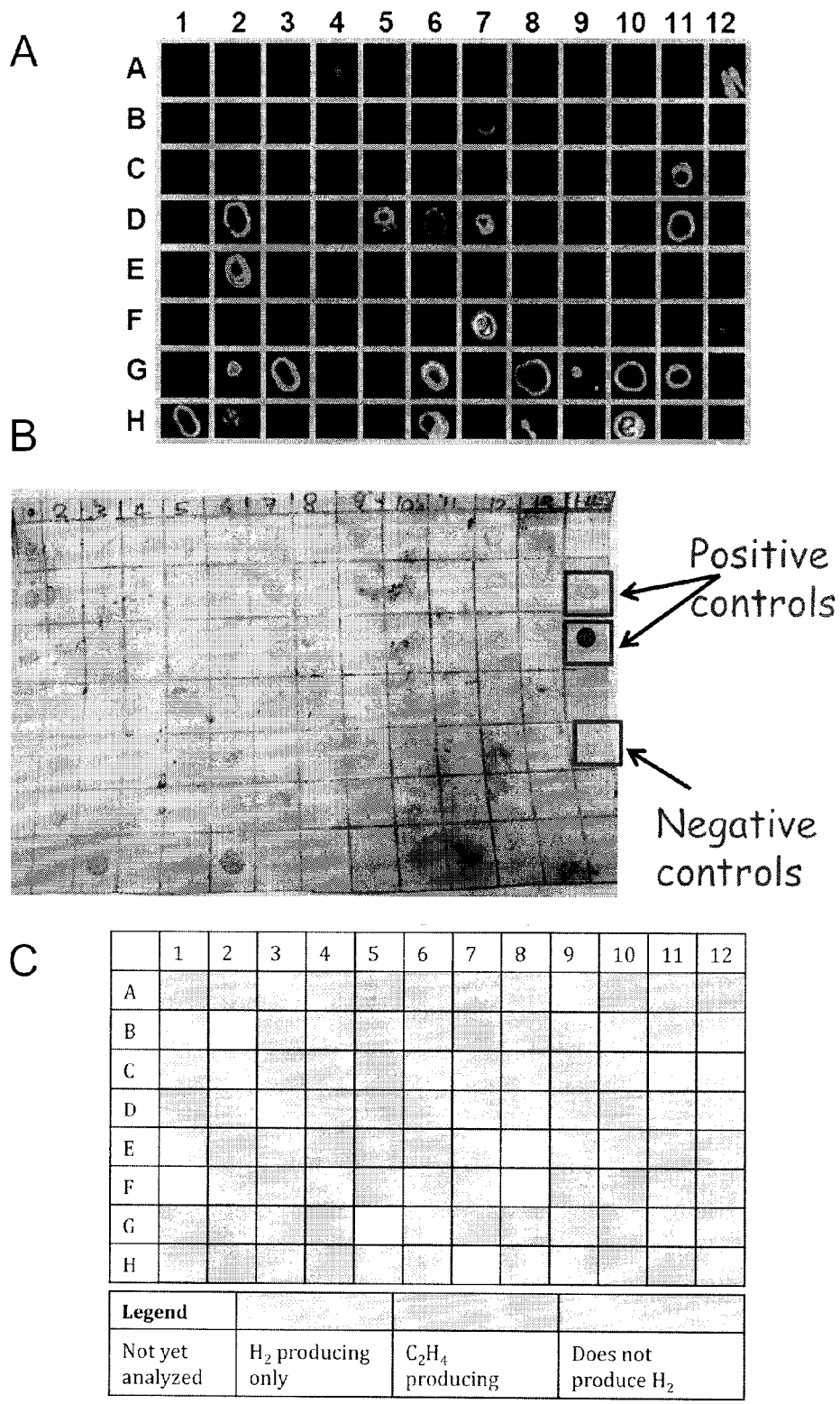

FIGS. 14A, B, and C show the validation of the glutamine biosensor to detect biological nitrogen fixation directly in microbial colonies on solid agar plates using an imaging camera. (A) GlnLux indicator agar was used to detect nitrogen fixation in maize bacterial endophytes. Shown are maize endophytes on GlnLux agar after incubation for 36 hrs. Images were taken using CCD camera using a 600 sec exposure. Colonies were scored from 0-5. (B) The same colonies as in panel A were used to extract genomic DNA, and then molecularly analyzed using Southern dot blot hybridization (nifH). Each sample was scored from 0-5. (C). Validation of GlnLux results using an acetylene reduction assay. Colonies were individually inoculated into tubes as overnight cultures, and the headspace (gas) was collected for analysis by gas chromatography for nitrogenase-mediated reduction of acetylene to ethylene as well as $H_2$ gas. As there was some disagreement between ARA and the dot blot, GlnLux correlation to both assays when pooled was examined.

Figure 15:
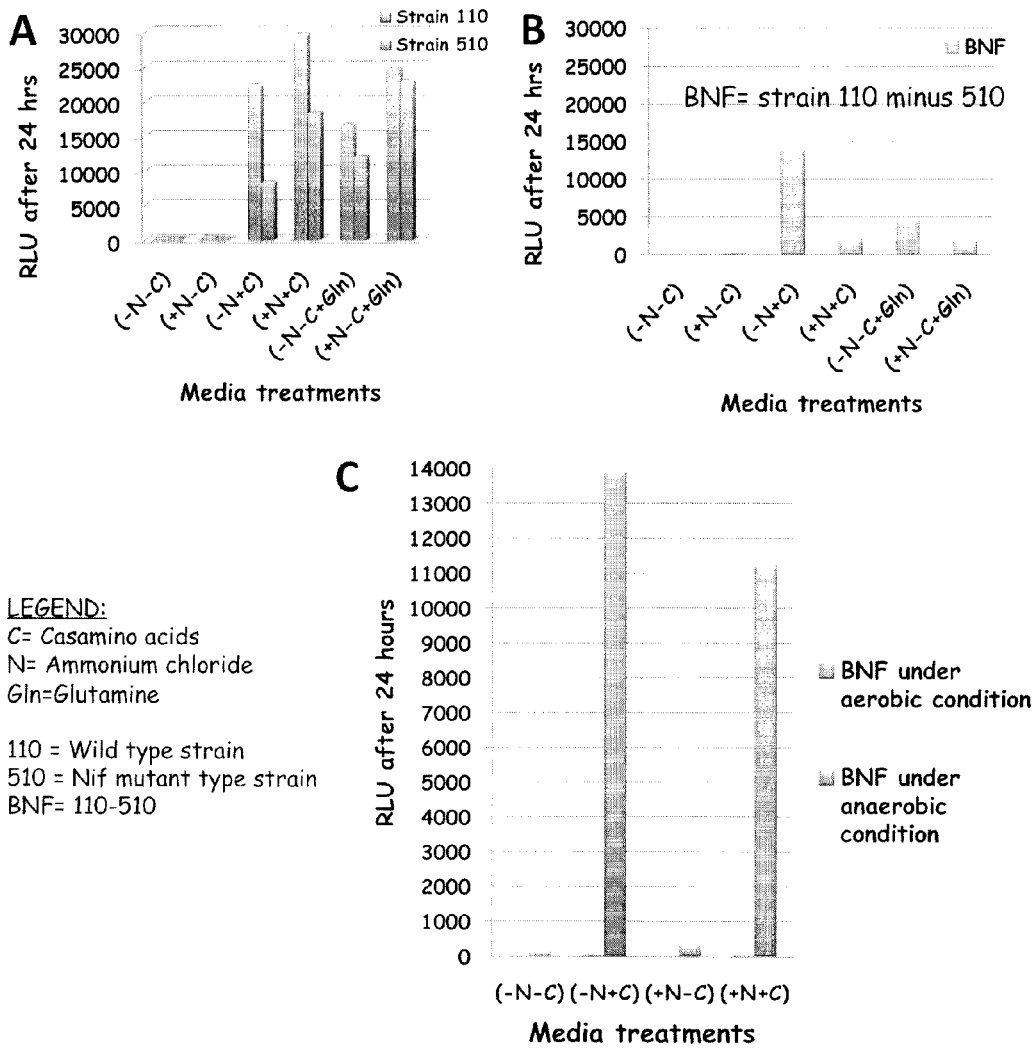

FIGS. 15A, B, and C show the use of a GlnLux liquid assay to measure nitrogen fixation in microbes quantitatively using a luminometer plate reader. (A) *Bradyrhizobium japonicum* strains (110 wild-type and 510 mutant) were pre-treated with casamino acids or glutamine (known to stimulate biological nitrogen fixation) or ammonium (known to repress biological nitrogen fixation), prior to co-incubation with GlnLux in 96-well plates. (B) To separate the direct effect of added amino acids in panel A on GlnLux, versus its detection of biological nitrogen fixation, the lux output of the wild-type strain 110 was subtracted from the derivative mutant strain 510 incapable of nitrogen fixation. The results were as expected if GlnLux could accurately measure biological nitrogen fixation. In panels A and B, *Rhizobium* cells were first incubated anaerobically at 37° C. for 6 days. (C) Effect of oxygen on nitrogen fixation. GlnLux could successfully detect the predicted effect of oxygen repressing biological nitrogen fixation (blue bars).

While the invention will be described in conjunction with example embodiments, it will be understood that it is not intended to limit the scope of the invention to such embodiments. On the contrary, it is intended to cover all alternatives, modifications and equivalents as may be included and defined by the appended claims.

DETAILED DESCRIPTION OF THE INVENTION

In general, nitrogen is the most limiting soil nutrient for plant growth globally. Nitrogen gas ($N_2$) in the atmosphere cannot be used directly by plants as a nitrogen source as it has a strong triple covalent bond and higher plants cannot break this bond. Nitrogen-fixing microbes (diazotrophs), however, are capable of converting atmospheric nitrogen to ammonia ($NH_3$) in a process termed biological nitrogen fixation (BNF). Ammonia can then be used by plants as a nitrogen source (16, 37). The microbial enzyme required for this reaction is nitrogenase. Biological nitrogen fixation requires electrons and protons in addition to significant amounts of ATP (19). The biological nitrogen fixation reaction can be represented as ($N_2+8H^++8e^-+16\ ATP\rightarrow 2NH_3+H_2+16\ ADP+16\ P_i$) (42).

Legumes and green manures are well known among crop plants for their ability to associate with microbes that fix nitrogen, known as diazotrophs. *Rhizobia* are well-known diazotrophs and are soil bacteria that undergo nitrogen-fixing symbiosis with leguminous plants. There are 44 identified species of nodule-forming bacteria on legumes. These species belong to the classes, Alphaproteobacteria, (*Allorhizobium, Azorhizobium, Blastobacter, Bradyrhizobium, Mesorhizobium, Methylobacterium, Rhizobium* and *Sinorhizobium*, and to the class Betaproteobacteria (*Burkholderia* and *Ralstonia*) (56). The biological nitrogen fixation microbes inhabit specialized plant organs, called nodules. These nodules are tumor-like structures which form as a result of root infection by the bacteria. Following infection, the bacteria differentiate into active nitrogen-fixing forms called bacteroids (endosymbiotic form of bacteria) (64, 65). These bacteroids are surrounded by a specialized plant membrane called the symbiosome membrane or the peribacteroid membrane. A symbiosome membrane represents a physical and functional interface between the plant and the bacteroid controlling exchange of metabolites. One infected root nodule cell may enclose thousands of bacteroids each surrounded by a symbiosome membrane. The symbiosome membrane with the enclosed bacteroid and symbiosome space (the space between the symbiosome membrane and bacteroid outer membrane) form the symbiosome (66, 67).

The relationship between the host plant and the bacteroid is known as a symbiotic relationship as both the plant and the bacteroid benefit. While nitrogen fixation by bacteroids provides ammonia, in return, the plant provides bacteroids with sugars for energy (64, 65).

Many important crops such as wheat, rice and maize, do not form nodules. However, it has been shown that diazotrophic endophytes that inhabit other grasses, such as cultivars of Brazilian sugar cane, can provide part of the plant demand for nitrogen from biological nitrogen fixation. An endophyte is a bacteria or fungus that inhabits plants without causing damage to its host. In the case of sugar cane, the major diazotrophs are *Gluconacetobacter diazotrophicus* and *Herbaspirillum* spp. which inhabit the stems and leaves, along with endophytes belonging to species of *Azospirillum* and *Burkholderia* (68). These endophytes are estimated to contribute up to 150 kg N ha$^{-1}$ year$^{-1}$ to sugar cane (68).

Mutant strains of *Rhizobium* with improved symbiotic nitrogen fixation activity were first reported in 1978 by Maier and Brill. This improvement was done by means of chemical mutagenesis. These mutants were effective but not competitive in soils with high indigenous *Rhizobium* populations. Later, improved *Rhizobium* strains were developed by chemical mutations and were preselected for competitiveness under field conditions (70). In general it has not been easy to distinguish spontaneous mutants from natural strain selection, especially because the most preferred method to select highly effective *Rhizobium* strain-host legume combinations is in planta using the host legume.

Using chemicals or radiation for mutagenesis can speed up the screening process as it increases the mutation frequency. The success in mutant screening depends mainly on the availability of an efficient screening procedure (70). Examples of chemical mutants that have been reported involve mutants capable of rapid or improved nodulation, higher nodule occupancy, expanded host range, nodulation in the presence of inhibitory levels of fixed N, and enhanced nitrogen fixation activity (70). Mutants having altered metabolism of cytochrome and molybdenum have been found to have enhanced nitrogen fixing activities while mutants having altered tryptophan metabolism, succinate metabolism, and lectin binding ability, have been found to have improved nodulation. The way that the altered metabolism may affect the mutant's ability to survive in field conditions is unknown (70).

Current technologies to detect biological nitrogen fixation include the acetylene reduction assay, the natural abundance N$^{15}$ labelling method, and growth on N free medium. The acetylene reduction assay (ARA) is the most commonly used method for detecting nitrogen fixation. This assay depends on the ability of nitrogenase to reduce acetylene gas ($C_2H_2$) to ethylene gas ($C_2H_4$) as represented in the reaction ($C_2H_2$+ 2H$^+$+2e$^-$ $\xrightarrow{\text{Nitrogenase}}$ $C_2H_4$) (71). In this method, the test sample is incubated in a tight container with a constant concentration of acetylene gas for a certain period of time. The ethylene gas produced from the reaction can be collected and quantified by gas chromatography. This assay is simple but expensive and generally not sensitive enough for quantification of biological nitrogen fixation (72).

The natural abundance N$^{15}$ labelling method relies on the fact that the abundance of N$^{15}$ in the atmosphere (and incorporated into biological nitrogen fixation-derived N) is different than from mineral/soil-derived N. Nitrogen can exist as two stable isotopes, N$^{15}$ and N$^{14}$. Analyzing plant samples for their N$^{15}$/N$^{14}$ ratio is thus a measurement of the contribution of plant N from biological nitrogen fixation. This method is favoured by plant scientists working under field conditions, but accurate estimates of biological nitrogen fixation require sampling both the shoot and root which can be challenging. The cost of this method is modest (~\$5-\$10 USD per sample) but it requires an experienced technician at a dedicated facility. For example, many Guelph researchers send plant tissue samples to Saskatoon for N$^{15}$ isotope analysis. In Costa Rica, plant samples are sent to California as no facility exists in Central America. Another major limitation of this assay is that it requires a reference non-nodulating plant with similar growth characteristics as the plant variety of interest, for ratio calibration. In the United States, a non-nodulating soybean genotype is used as the reference plant for measurements of soybean biological nitrogen fixation. However, such reference genotypes are not available for many legumes and green manures, which perhaps contributes to some researchers referring to this method as insensitive and inaccurate (72).

The growth on N free media method simply involves streaking test colonies on plates of nitrogen free media and then incubating the plates at the suitable growth temperature and observing growth. Colonies that can grow on nitrogen free media are more likely capable of fixing nitrogen. This method is simple and cheap but insensitive.

The most common methods to quantify plant Gln often involve HPLC analysis of tissue extracts (43, 47) or chlorophyll-based assays (e.g. SPAD meter) for use in intact plants as indirect indicators of Gln (4, 23, 24, 53). Though the former method is accurate, it requires analytical chemistry expertise; the latter method is indirect and examines a late symptom of nitrogen deficiency. Neither HPLC nor chlorophyll measurements permit real time plant imaging.

Using the methods described herein, the glutamine biosensor assay was able to quantify Gln in plant tissue extracts using a rapid aqueous extraction procedure from as little as 1 mg of tissue. GlnLux output was found to highly correlate with traditional HPLC-based quantification of Gln in plant tissue extracts. Furthermore, GlnLux embedded in agar (GlnLux-agar) permitted CCD imaging of Gln in intact plant organs, at a sensitivity threshold of 0.01-0.1 mM Gln. Both assays were sufficient to distinguish whether or not seedlings had been fertilized with nitrogen.

Furthermore, spatial imaging of mature leaves using GlnLux-agar suggested that the highest Gln concentration was at the leaf base, in the midvein region, consistent with Gln being scavenged for export to growing organs (metabolic sinks), and in agreement with both spatial HPLC analysis (8) and expression of glutamine synthetase mRNA and protein (30, 35).

In the Examples shown below, the accuracy of the glutamine biosensor was validated for quantifying Gln using Gln standards, as well as free Gln levels in plants, both using a visualization approach as well as liquid assays involving a luminometer. The data also shows that the glutamine biosensor could distinguish plants that had received nitrogen fertilizer as compared to fertilizer lacking nitrogen, which has implications for the use of the technology described herein for measuring soil nitrogen and as a diagnostic technology for nitrogen fixation.

It will be shown below that the glutamine biosensor described herein is an alternative to the above technologies that is, in aspects, non-destructive, inexpensive, high-throughput, and accurate. The glutamine biosensor also permits phenotyping of plants early in the growing season. Two further exemplary in planta applications of the glutamine biosensor include:

1. Screening inoculants for nitrogen fixing ability or capacity: for those legumes or other plants that export fixed nitrogen in the form of amino acids, then following inoculation with candidate microbial nitrogen fixing inoculants, non-destructive leaf punches can be assayed using the glutamine biosensor to quantify amino acid export from nodules, compared to plants inoculated with non-nitrogen fixing microbial strains.
2. Screening for nitrogen fixation efficiency in nodules, which are root-derived organs that host nitrogen fixing bacteria. In this application, nodule sections (or individual nodule extracts) may be incubated with the glutamine biosensor to determine nitrogen fixation within the nodules themselves.

The goal of either of the above approaches would generally be to select for the most compatible and efficient nitrogen fixing microbial strain for each plant genotype including new plant varieties that are released into each new environment (each genotype (G)×environment (E) combination). In this way, nitrogen fixation can be improved on a case by case, crop by crop, or plant by plant basis depending upon the actual genotype of the plant and the environment in which it grows.

Supporting evidence that the glutamine biosensor described herein can distinguish different concentrations of free organic nitrogen in planta, in young plants, even under field conditions which are relatively uncontrolled is shown in Example 5, described below in detail. Quantitative differences in available nitrogen can be determined by using leaf punches applied to a screening medium containing the glutamine biosensor. The implication of these results is that leaf punches of plants, when placed on medium containing the glutamine biosensor, could be used to test the compatibility and efficiency of different microbial strains for fixing nitrogen, as these strains will affect the Gln (and amino acid) content in shoots.

As used herein, "whole cell biosensor" or "biosensor" means a microbial cell used to detect an analyte or stimulant of interest. A "glutamine biosensor" is thus a microbial cell that is used to detect glutamine. For example, the whole cell biosensor may respond to a specific analyte or condition and is created by fusing a reporter gene to a promoter which is in turn regulated by a specific analyte, condition, or some sort of stress. It is known that a subset of microbial biosensors have been based on auxotrophs expressing a constitutive reporter such as green fluorescent protein, luciferase, etc. An auxotroph is an organism that cannot grow in the absence of a particular metabolite. The use of amino acid auxotrophs for the quantification of some bioavailable essential amino acids such as lysine in human and animal foodstuffs is known (6, 7, 18, 26, 48, 60). A specific example of a whole cell biosensor is a lux-expressing Gln auxotroph, referred to as "GlnLux", which expresses the reporter lux in the presence of Gln.

For the purposes of the present invention, "growth medium" or "growth media" means a liquid, gel or solid medium designed to support the growth of microorganisms. Such media include, but are not limited to nutrient broths such as Lysogeny Broth (LB), M9 medium and agar plates. It will be understood that any other suitable media for microbial growth may be used. Liquid media such as LB and M9 are often mixed with agar and poured into Petri dishes to gel or solidify. These agar plates provide a gel-like or solid medium on or in which microbes may be cultured.

"Inoculant nitrogen-fixing microbe" means microbes, microbial cells, or microbial strains that are used as inoculants. For the purpose of the present invention, "inoculant" means a microbial inoculant, plant inoculant or soil inoculant. An inoculant is commonly known as a beneficial microbe (bacteria, archaea, or fungi) or a combination of many beneficial microbes which promote plant health. While microbial inoculants are generally applied to improve plant nutrition, they can also be used to promote plant growth and act as biofertilizers. The rhizobacteria commonly applied as inoculants include nitrogen-fixers and phosphate-solubilisers which enhance the availability of the macronutrients nitrogen and phosphorus to the host plant. They are beneficial for nitrogen fixation and plant nutrition. Such bacteria are commonly referred to as plant growth promoting rhizobacteria. *Rhizobium* are commonly used as inoculants for leguminous crops; *Azospirillum* for non-leguminous crops; and diazotrophic rhizobacteria for cereal crops.

Therefore, for the purposes of the present invention, the expression "inoculant nitrogen-fixing microbe" includes, without limitation, *Rhizobium*, other endophytes, and diazotrophic bacteria such as *Azospirillum*.

For the purposes of this invention, the term "plant" is defined in its broadest sense and means living organisms belonging to the kingdom Plantae and includes organisms such as trees, flowers, herbs, bushes, grasses, vines, ferns, mosses, green algae and plant material (forage including grasses, legumes, silage and crop residue).

"Plant organ" means a functional and structural unit of a plant. For the purposes of the present invention, the expression "plant organ" will be used interchangeably with the expression "plant tissue", and will include, without limitation, a plant root, stem or leaf and clippings thereof, such as a leaf punch.

"Seed" means the embryo of a plant. A seed is usually enclosed in a covering or seed coat. The term "seed" means anything that can be sown; in some cases what is sown is the seed enclosed in the seed coat (shell or hull, or a tuber).

"Soil" means a natural resource made up of minerals that come from rocks, organic matter which is the remains of plants and animals that use the soil, and the living organisms that reside in the soil.

"Quantifying" means to measure or assess the quantity of. For the purposes of the present description, a plate reader or luminometer was used to visualize, identify, screen, detect or quantify a signal corresponding to the expression of the constitutive lux reporter of the Gln biosensor or glutamine levels, as described in the examples below. However, it will be understood that other methods of quantification are within the scope of the present invention.

A medium that is "essentially free of glutamine" or is "glutamine-depleted" is a medium that is either completely free of glutamine or has a small amount of glutamine that does not interfere with the signal produced by the glutamine biosensor as would be understood by one of skill in the art. For example, if glutamine is present in the medium in a small amount or completely absent, the background amount of signal from the glutamine biosensor will be low. This provides an improved signal to noise ratio when assessing the signal from the biosensor in the presence of a glutamine-containing analyte, such as a microbe or plant portion.

The medium described herein comprises an essentially glutamine-free growth medium and a glutamine biosensor. The growth medium may be any medium in which the glutamine biosensor is capable of growth. For example, the growth medium may be LB or M9 medium, in a specific aspect M9 medium, with or without agar. The medium is essentially glutamine-free, so that there is little to no signal emitted from the glutamine biosensor unless a glutamine-containing analyte, such as a plant portion or microbe, is added to the medium.

The glutamine biosensor is a bacterial culture that emits a signal in the presence of glutamine. In order to emit a signal in the presence of glutamine, generally a glutamine auxotroph is used, meaning a cell that requires glutamine for growth. A glutamine auxotroph can be made by downregulating glutamine synthetase in the cell as compared to a wild type cell and then by inserting into the cell, using known methods such as transfection or transduction, a reporter gene that is expressed when glutamine is added to the cell culture medium.

The glutamine biosensor is, in one aspect, a culture of *E. coli* cells that have been engineered to express a Lux signal in the presence of glutamine, such as the GlnLux strain described below. In an aspect, the medium comprises about 10% v/v of a solution containing the glutamine biosensor, wherein the solution containing the glutamine biosensor has an $OD_{595}$ of from about 0.001 to about 10.0, or any range or amount in between. However, the medium may comprise any amount of the glutamine biosensor, such as from about 1% to about 90% v/v of the glutamine biosensor and any range or amount in between.

In a particular aspect, when agar is used as the medium, the medium comprises about 10% v/v of a solution containing the glutamine biosensor, wherein the solution containing the glutamine biosensor has an $OD_{595}$ of about 1.0. In another particular aspect, when the medium is a liquid medium, the medium comprises about 10% v/v of a solution containing the glutamine biosensor, wherein the solution containing the glutamine biosensor has an $OD_{595}$ of about 0.025.

The glutamine biosensor is not limited to being a culture of *E. coli* cells and may be any microbial culture that can be engineered to respond to the presence of glutamine by producing a signal. Suitable cultures would be well known to a skilled person, as well as glutamine-responsive promoters and reporters.

Similarly, the signal produced by the glutamine biosensor may be any type of signal identifiable by a skilled person. The signal may be a type that is readable on a luminometer, or the signal may be visible to the naked eye. The signal may be quantitative or qualitative, providing an actual measurement of glutamine or a "yes" or "no" answer as to the presence of glutamine. For example, the signal may be based upon bacterial luciferase (lux), firefly luciferase (luc), or green fluorescent protein (GFP) as reporter genes. Any other reporter gene known that can be coupled to a Gln-responsive promoter to emit a signal in the presence of Gln may be used.

The medium may include other components, such as, for example, protease inhibitors or amino acids. In one embodiment, the medium includes a protease inhibitor cocktail and casamino acids, which are a mixture of amino acids and some very small peptides obtained from acid hydrolysis of casein. Other components that may be included in the medium comprise buffers, excipients, diluents, proteins, lipids, small molecules, pharmaceutical agents, growth enhancing compounds, nutrients, and so on.

In plants, nitrogen fertilizer is assimilated into Gln (12, 39) and subsequently glutamate; together, these amino acids serve as nitrogen donors for various reactions, including the biosynthesis of other amino acids (34, 39). These amino acids further regulate uptake and assimilation of soil nitrate and ammonium (13, 25, 29, 40, 61). As Gln is an important form of nitrogen used for long-distance transport in the plant, including from root to shoot (49), it is a key indicator of the status of nitrogen levels in plants.

Levels of free Gln are an early indicator of whether a plant is receiving sufficient nitrogen fertilizer for optimal growth (46). Specifically, the concentration of shoot Gln indicates the availability of nitrogen around roots as well as a plant's ability to uptake, biochemically assimilate and appropriately transport nitrogen (22). Therefore, the medium described herein is useful in methods of determining the nitrogen content of plants and plant portions or extracts.

Thus, the medium and biosensor of the invention may be used to detect glutamine and therefore nitrogen within a microbe, soil, or plant tissue. The medium and biosensor may also be used to predict plant efficiency in absorbing and assimilating soil nitrogen and/or in scavenging nitrogen from senescing plant cells.

It has been demonstrated herein that a medium comprising a glutamine biosensor can be used effectively to culture, identify, screen for, select, or detect nitrogen-fixating microbes as well as the glutamine content (and therefore, by proxy, the nitrogen content) within analytes such as plant materials or extracts. The glutamine biosensor is a cell that has a reporter gene coupled to a Gln-responsive promoter, so that the glutamine biosensor will report a signal in the presence of glutamine. The medium is essentially glutamine-free and is therefore referred to as glutamine-free or glutamine-depleted medium. Because the medium is essentially glutamine-free, a signal is only seen when an analyte comprising glutamine is placed in or on the medium.

The invention thus provides methods of determining the nitrogen content in an analyte of interest, such as a plant material. The plant material is placed on or in the glutamine-depleted medium comprising a glutamine biosensor and is incubated for a period of time. If glutamine and, therefore, nitrogen is present in the plant material, the glutamine biosensor emits a signal. The signal may be evident to the naked eye, or a luminometer, for example, may be used to detect the signal. The signal may be qualitative, in that it provides an indication of the presence or absence of glutamine or the signal may be quantitative and provide a measurement of the amount of glutamine by comparing the emitted signal to a standard.

The analyte of interest may be, for example, at least a portion of a plant, a plant organ, a seed, soil, or an extract thereof. Examples of plants that may be used as an analyte of interest include, but are not limited to, legumes and cereals. Exemplary legumes include alfalfa, peas, beans, lentils, lupins, mesquite, carob, soybean, cowpeas, and peanuts. Exemplary cereals include maize (corn), rice, wheat, barley, sorghum, millet, oats, triticale, rye, buckwheat, fonio, and quinoa. Plants that may be used also include green manures. Green manures in this context may include, for exampleclover, vetch, sesbania, and velvet beans.

The analyte of interest may also be a microbe or an extract thereof. Examples of microbes that may be analyzed for nitrogen fixation capacity or ability are classified as diazotrophs. Specific examples of diazotrophs include bacteria in the class Alphaproteobacteria, (e.g., *Allorhizobium, Azorhizobium, Blastobacter, Bradyrhizobium, Mesorhizobium, Methylobacterium, Rhizobium* and *Sinorhizobium*), and to the class Betaproteobacteria (e.g., *Burkholderia* and *Ralstonia*). Other examples of diazotrophs include cyanobacteria, green sulfur bacteria, Azotobacteraceae, and Frankia.

The present methods also provide a quick and easy technique for determining whether or not the soil being used requires fertilization to support the growth of a plant. For example, a clipping may be obtained from a plant growing in the soil. The clipping is placed in the glutamine-depleted medium comprising the biosensor and is incubated for a period of time. After this time, the medium is examined for a signal from the biosensor. If a signal is present or is above a certain pre-determined level, this would be an indication that the soil contains sufficient fertilizer to support the growth of the plant. If the signal is not present or is below the pre-determined level, this would be an indication that the soil requires fertilization.

The analyte, such as the plant material or microbe, is incubated in the medium for a period of time sufficient to show a signal if glutamine is present in the analyte. For example, the analyte may be incubated in the medium for from about 1 minute to about 35 hours and any amount or range in between, such as about 10 minutes, or from about 8 hours to about 22 hours. In one aspect, the analyte is incubated in the medium for about 1 hour. The desired amount of time can be determined by the end user and depends upon the analyte being tested.

The methods described herein may be carried out in a lab or in the field or may be a combination method, wherein a sample is obtained in the field and then sent to a lab for analysis. Thus, in an aspect, there is provided an assay or kit for determining biological nitrogen fixation in an analyte, wherein the assay comprises the medium containing the glutamine biosensor. The assay may further include a machine for detecting a signal, if the signal is not evident to the naked eye, such as a CCD camera or a luminometer. A detectable signal, or a signal with an intensity above a predetermined level or threshold, is indicative of nitrogen fixation in the analyte. Alternatively, the assay be provided together with a mail-in label or package for shipping the completed assay to a secondary location, such as a laboratory, to read and interpret the results. In this way, no special knowledge or equipment is required by the end-user to operate or read the assay. The assay may also be provided together with instructions for use. Alternatively, instructions for use may be provided on a website, for example.

The methods may be conducted at any temperature above about 4 degrees Celsius, but are desirably carried out at temperatures between about 15 and 42 degrees Celsius or any range or degree therein between.

When the analyte is plant tissue, as little as about 1 mg plant tissue, diluted about 1000-fold in water, may be used. Larger sized samples may be used but this small sample size permits detection of the nitrogen status in a plant with minimal destruction to the plant itself. Dilution is not required, but may improve sensitivity and specificity, as would be understood by a skilled person. In aspects, the amount of plant tissue used is from about 0.1 to about 1000 mg, from about 1 to about 100 mg, from about 1 to about 50 mg, from about 1 to about 20 mg, or from about 1 to about 10 mg, or any amount or range in between. In another aspect, the amount of plant tissue used is the amount that would be obtained from a leaf punch of about 1 cm in diameter. Generally, a leaf punch is used as it is not damaging to the plant itself yet provides sufficient material to apply to the assay and test with the glutamine biosensor. The plant tissue may be used as is or it may be diluted from about 2 to about 2000-fold or from about 100 to about 1000 fold, or any amount or range in between.

EXAMPLES

Without intending to be limiting in scope, the following examples serve to illustrate various embodiments of the invention.

Glutamine is a critical intermediate in nitrogen metabolism in all organisms. Here, a whole cell biosensor (GlnLux) for glutamine (Gln) was constructed by transforming a bacterial Gln auxotroph with a constitutive lux reporter. The biosensor was modified to improve sensitivity, linearity, efficiency, specificity, and robustness to permit detection of Gln in vitro and in vivo. The GlnLux biosensor achieved nanomolar sensitivity with Gln standards. Extracts from only 1 mg of maize (*Zea mays* L.) leaf tissue were sufficient for Gln detection by GlnLux. Measurements of Gln in leaf extracts by GlnLux correlated with quantification by HPLC (Spearman r=0.95). GlnLux permitted indirect in planta imaging of Gln using a CCD camera, enabling identification of plants that had been fertilized with nitrogen. Imaging using GlnLux also resolved predicted spatial differences in leaf Gln concentration.

Example 1

Improvement of a Gln Biosensor Through Liquid Extract Quantification

This example shows the creation of a lux-expressing Gln auxotroph that is a sensitive whole cell biosensor for Gln (GlnLux). This GlnLux biosensor allowed both liquid extract quantification and visualization of free Gln in plants.

SUMMARY

A Gln auxotroph of *Escherichia coli* was generated by down-regulation of the gene encoding glutamine synthetase (GlnA). Therefore, a microbial whole cell biosensor for Gln was constructed based on the *E. coli* GlnA auxotroph obtained from the *E. coli* Genetic Resource Center (CGSC#10775, Yale University, U.S.A.), and subsequently transformed with a constitutive lux reporter (hereinafter referred to as "GlnLux", "GlnLux biosensor" or "Gln biosensor"). More specifically, the Gln-auxotrophic *E. coli* strain (JW3841-1, $Kan^R$) was obtained from the *E. coli* Genetic Resource Center and was generated by inserting a kanamycin cassette into GlnA [glnA732(del)::kan] (2). The strain was transformed with Ampicillin-resistant plasmid pT7-lux (37) containing a constitutive T7 promoter from *Xenorhabdus luminescens* driving the luxCDABE operon from *Vibrio fischeri* to create a strain GlnLux.

Figure 1:
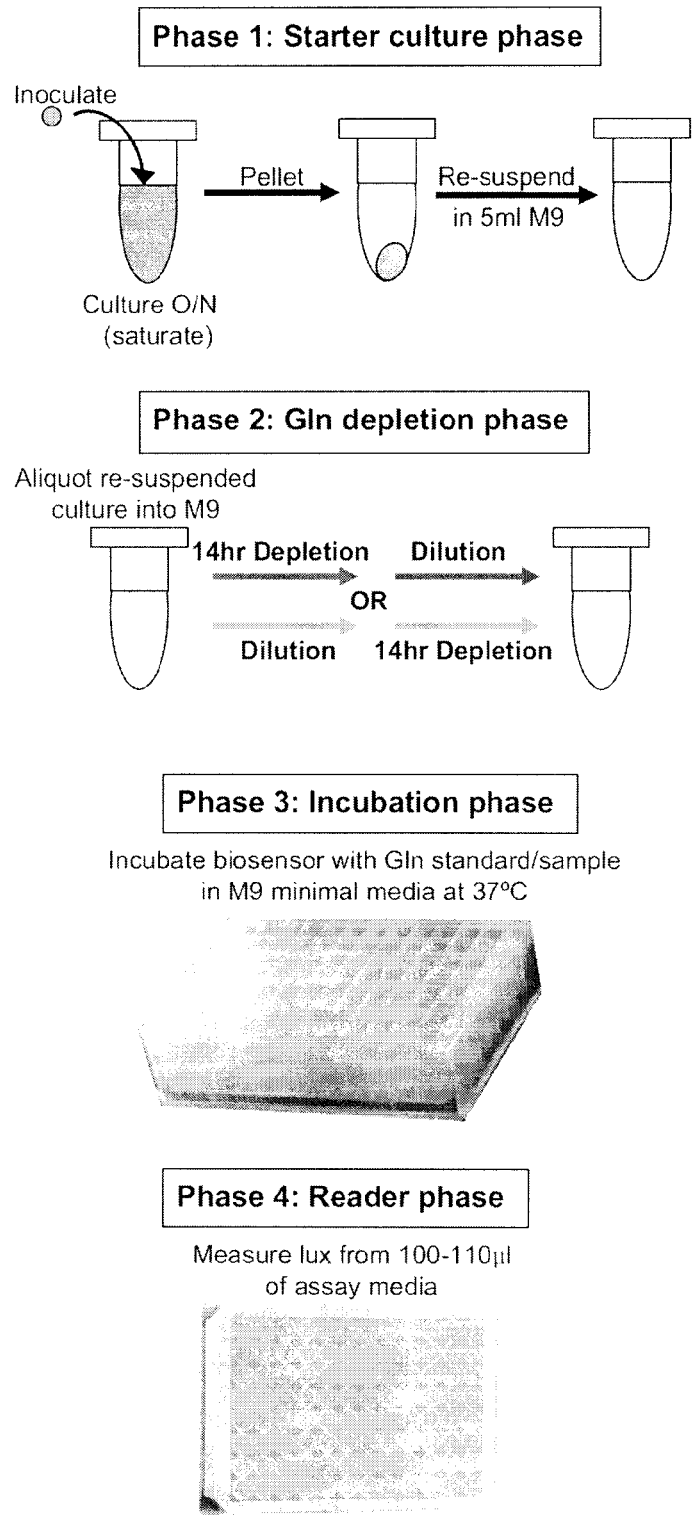
FIG. 1 is a flowchart depicting the methodology used for quantification of free Gln using GlnLux in liquid assays. In Phase 1, GlnLux cells are multiplied in LB medium, washed and resuspended in Gln-free M9 minimal medium. In Phase 2, GlnLux cells are diluted and then incubated in M9 minimal medium to deplete endogenous free Gln. In Phase 3, GlnLux cells are incubated with Gln standards or tissue extracts containing free Gln. In Phase 4, lux output was read hourly in a 96-well luminometer in replicates of 3-4, randomized across 3-4 plates.
Figure 2:
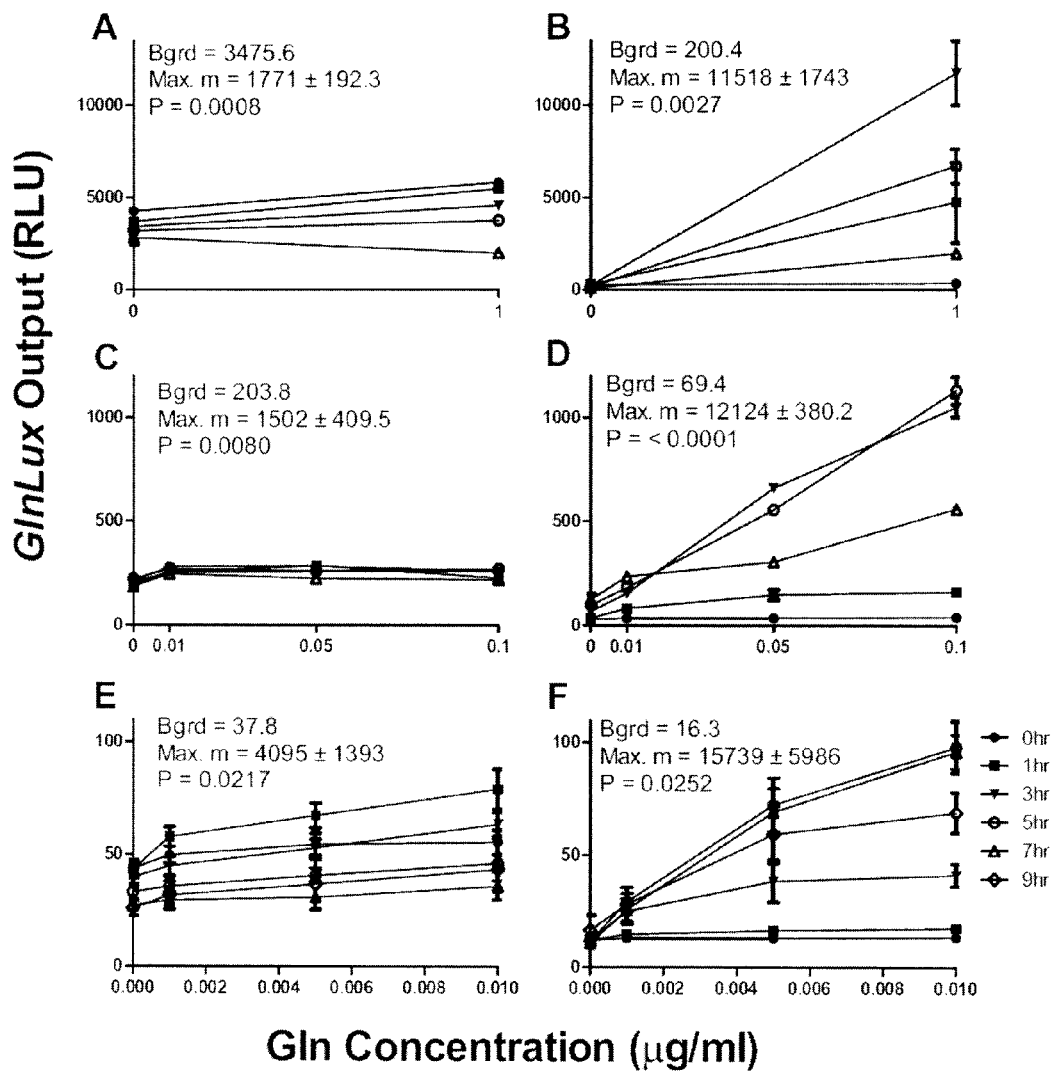
FIG. 2A to 2F show the pre-assay improvement and the effect of diluting GlnLux cultures relative to background noise and sensitivity of the luminometer assay. GlnLux cell cultures are diluted in Phase 2 to the following optical densities ($OD_{595}$) prior to depletion of endogenous Gln: (A) 0.25; (B) 0.025; (C) 0.025; (D) $1/10^{th}$ dilution of 0.025; (E) $1/10^{th}$ of 0.025; (F) $1/100^{th}$ of 0.025. As assay sensitivity improved, lower concentration ranges of Gln were tested. Plotted are the means of 3 replicates along with the SEM. Bgrd is the background lux output from GlnLux at 0 μg/ml Gln. Max m is the slope of the most sensitive lux response curve at the low Gln concentration range. P is the probability that Max m significantly deviates from zero. RLU means relative light units.
Figure 9:
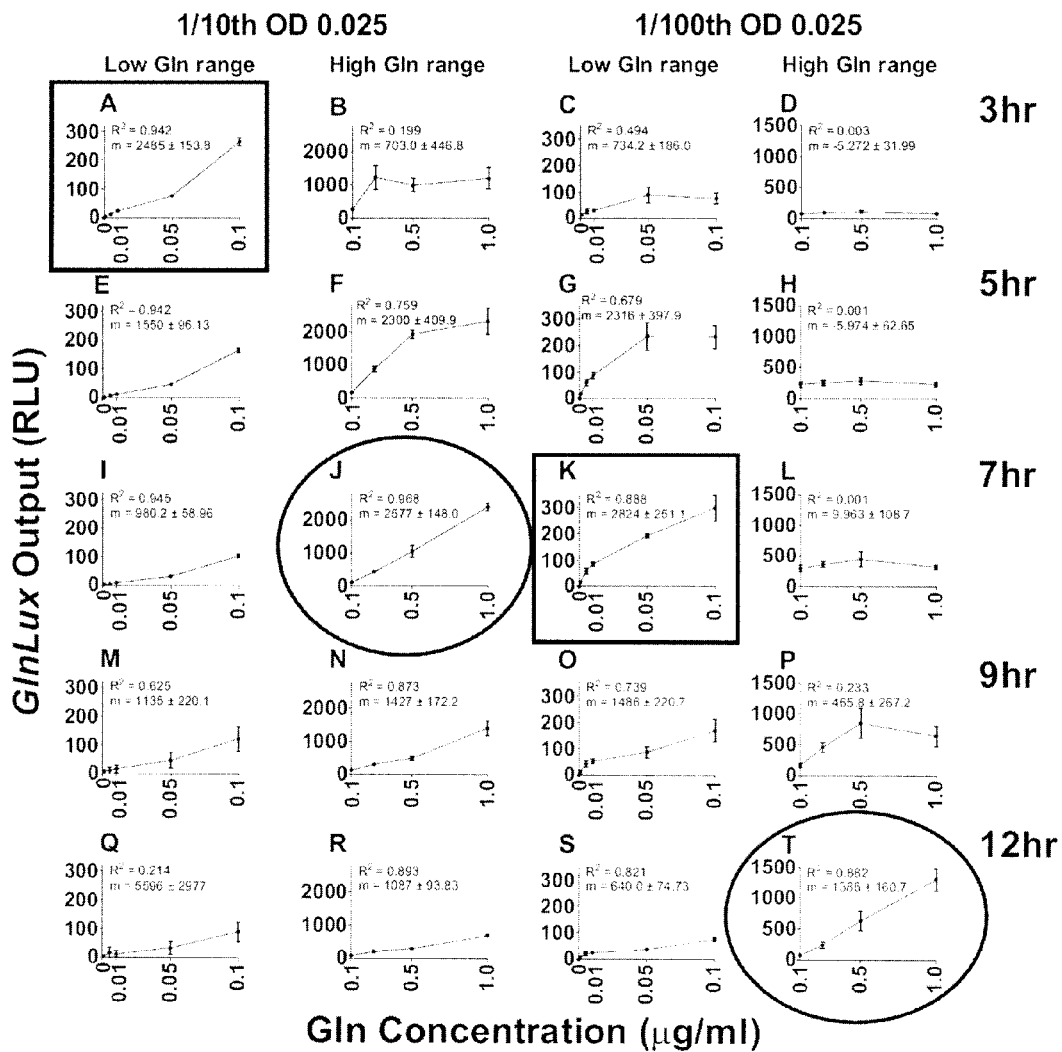

Five criteria are considered when determining the efficacy of a biosensor: linearity, sensitivity, specificity, robustness and efficiency (51, 57). As is shown in the experiments below, the GlnLux biosensor was found to be linear over four orders of magnitude (FIG. 3) and the linear range could be shifted simply by altering its incubation time with Gln (FIG. 9). With respect to sensitivity, a problem for conventional whole cell biosensors is background noise when the analyte of interest is also endogenous. In this example, native Gln was pre-depleted in GlnLux cells by incubating in M9 minimal medium, rendering the medium essentially glutamine-free. Assay sensitivity (signal:noise ratio) was also improved by diluting the GlnLux culture with the theory that with reduced cell counts, there would be more exogenous Gln available per cell, increasing the ratio of exogenous to endogenous Gln (FIG. 2). Using these strategies, the GlnLux biosensor achieved a sensitivity of 0.0001 µg/ml (0.68 nM) using a pure Gln standard (FIG. 3), in a similar range as the most sensitive HPLC-MS/MS (17, 21).

Figure 4:
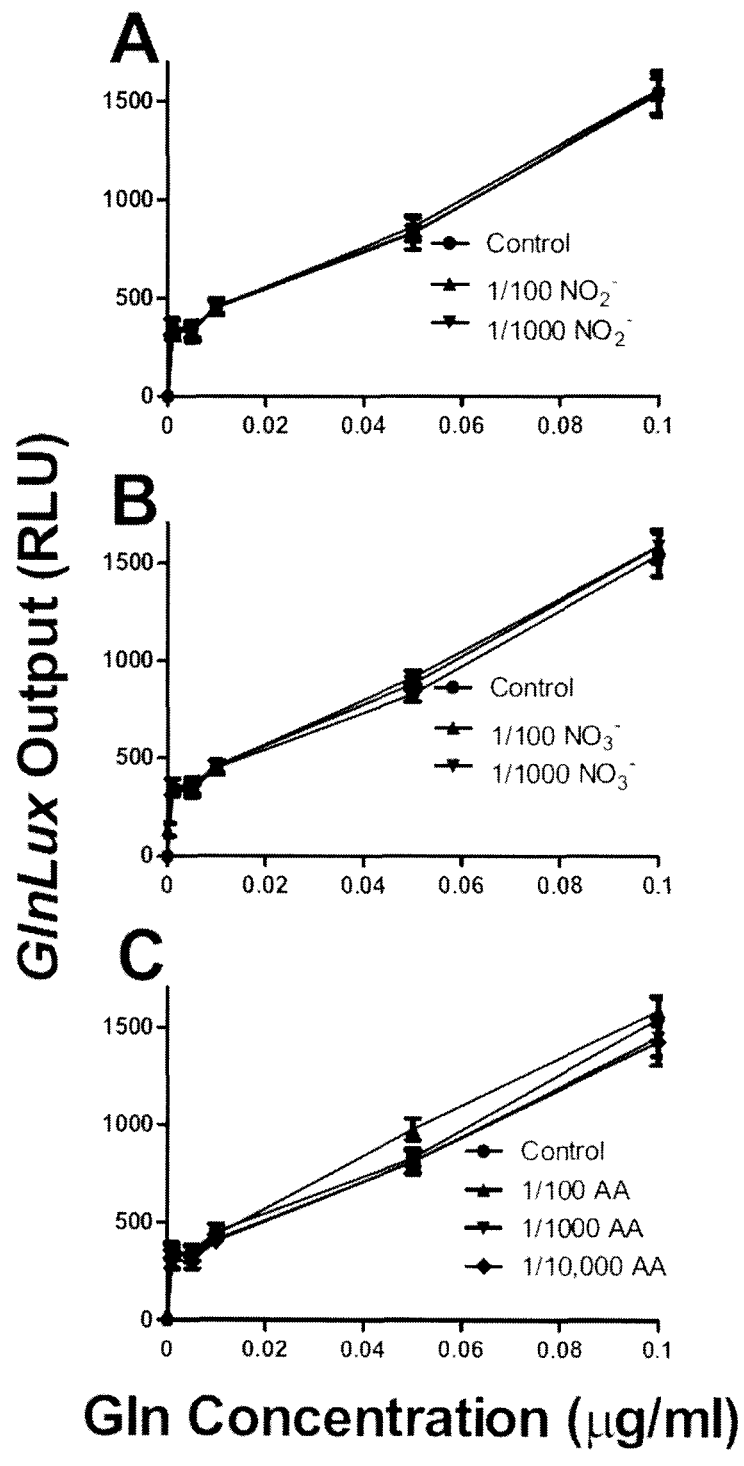

Another typical disadvantage of conventional biosensors is a lack of specificity when measuring biological samples. The present GlnLux biosensor has good sensitivity, leading to good specificity, as its use allowed the dilution of tissue extracts 1000-fold, thus reducing levels of potential interfering compounds, while still inducing a sufficient lux signal (FIG. 4). Apart from specificity, a challenge of using a conventional whole cell biosensor to measure biological samples is the presence of endogenous biological agents (e.g. enzymes) that vary unpredictably and interfere with assay reproducibility. Only free Gln was measured in the experiment set out below and, therefore, protease inhibitor was added to counter the effects of amino acid-liberating native proteases, increasing the robustness of the assay (Table 2). The improvement demonstrated below resulted in a GlnLux biosensor that was more linear, sensitive, specific and robust when using tissue extracts. It would be expected that the strategies set forth above and exemplified below would be applicable to other auxotroph-based biosensors.

Materials and Methods

Plasmid and bacterial strains. A Gln-auxotrophic *E. coli* strain (JW3841-1, Kan$^R$) was obtained from the *E. coli* Genetic Resource Center (CGSC#10775, Yale University, USA); it was generated by inserting a kanamycin cassette into GlnA [glnA732(del)::kan] (2). The strain was transformed with Ampicillin-resistant plasmid pT7-lux (37) containing a constitutive T7 promoter from *Xenorhabdus luminescens* driving the luxCDABE operon from *Vibrio fischeri* to create the strain GlnLux, also referred to as GlnLux or the Gln biosensor.

Media. The general bacterial growth media used was LB medium. The LB medium consisted of 5 g/liter NaCl (Fisher BP358-212), 5 g/liter yeast extract (Fisher DF0127179) and 10 g/liter tryptone (Fisher BP1421-500), with or without 12 g/liter Bacto-Agar (BD, DF0140010), pH 7.2. M9 minimal medium consisted of 22.2 mM D-(+)-glucose (Sigma G5767), 0.1 mM CaCl$_2$ (Fisher C-79), 2 mM MgSO$_4$ (Sigma 230391), and 1×M9 Salts, pH 7.0. A 5×M9 salt mix contained 0.24 M Na$_2$HPO$_4$ (Fisher S374B), 0.11 M KH$_2$PO$_4$ (Fisher P-284), 0.04 M KH$_2$PO$_4$ (Fisher BP358-212) and 0.09 M NH$_4$Cl (Sigma A-0171). All liquid and solid plate media, including visualization agar, was supplemented with 50 µg/ml kanamycin monosulfate (PhytoTech K378) and 100 µg/ml carbenicillin disodium salt (PhytoTech C346).

96-Well Luminometer Assays—Starter Culture (Phase 1). Biosensor strain GlnLux was inoculated into 15 ml of LB in a 50 ml Falcon tube, and grown overnight at 37° C. with shaking at 250 rpm. The culture was spun down at 700×g at 21° C. for 10 min. The supernatant was decanted and the culture was washed 3× in sterile M9 minimal medium with centrifugation as above, then resuspended in 15 ml sterile M9 minimal medium to the desired optical density (OD$_{595nm}$, range=0.25 to 0.025). In the modified protocol, the OD$_{595nm}$ used was 0.025 or dilutions thereof.

96-Well Luminometer Assays—Gln-Depletion Phase (Phase 2). Following Phase I, the resuspended GlnLux culture in M9 minimal medium (15 ml in a 50 ml Falcon tube) was incubated at 37° C. with shaking at 250 rpm for 0-24 h (as noted) to deplete any endogenous Gln. The culture was diluted up to 100-fold in M9 minimal medium either before or after the 14-h depletion (as noted in each figure). In the modified protocol, the starter culture (OD$_{595nm}$=0.025) was depleted for 14 h, and then diluted 10-fold prior to Phase 3. Carbenicillin and kanamycin were added at all stages.

96-Well Luminometer Assays—Gln Incubation Phase (Phase 3). To test the biosensor response to exogenous Gln or other compounds, the depleted GlnLux culture from Phase 2 was aliquoted initially into 96-well deep plates (Corning 3960) as follows: 180 µl of culture was added to 1620 µl of M9 minimal medium containing Gln standards (L-glutamine, PhytoTech G229) and any additional supplements (amino acids, sucrose, nitrate, nitrite; see below). To generate Gln standard curves, 0.2 M Gln stocks in ddH$_2$O were aliquoted and frozen at −20° C. until just before use. The stocks were serially diluted 500-fold in minimal M9 medium to 5 µg/ml Gln, and further serially diluted to generate standard curves. Every 96-well plate had at least one standard curve row (single replicate), with four replicates distributed across all assay plates. The deep-well plates were covered with a sterile breathable film (Sigma A9224) and incubated at 37° C. with shaking at 250 rpm. For Phase 4, aliquots were removed into 96-well shallow lux reader plates hourly as noted.

In the modified protocol, deep well plates were not used; instead, the incubation was performed in 96-well lux reader plates directly (see below) using 10 µl of GlnLux culture added to 90 µl of M9 minimal medium containing Gln standards. The plates were incubated at 37° C. without shaking.

96-Well Luminometer Assays—Luminescence Quantification (Phase 4). For lux quantification, initially 110 µl aliquots from each Phase 3 deep well plate were removed from each well and transferred to an opaque white 96-well plate (Fisher CS003912) and read in a MicoLumatPlus LB96V luminometer with WinGlow Software (Berthold Technologies, Germany). Samples were read for 1 s with a chamber temperature of 37° C. in an endpoint assay set to Integrate function. In the modified protocol in which the same opaque reader plates were used both for incubation (Phase 3) and lux quantification, there was no need to remove aliquots for hourly reads; instead, the plates were transferred back and forth from a 37° C. incubator, and the breathable film was replaced following each read. The assay media blank was subtracted for pre-assay modifications. Subsequently, readings of the zero-Gln standard in wells containing GlnLux cells, were subtracted from all lux values shown. Shown is the mean value of three to four replicates consisting of parallel incubations of Gln/extract with GlnLux cells randomized onto three to four incubation/reader plates.

Testing of Biosensor Specificity in Luminometer Assays. To test for the specificity of the GlnLux biosensor, concentrations of nitrogenous compounds present in plants were first determined from the literature. Nitrate levels in maize and related grasses range from 1-75 mM in stems, roots and leaves (31, 41, 45, 58). Nitrite levels in plant tissues have been reported to range from 0.36-1.39 µg/ml in stem sap (58). Each of the 19 other major amino acids range in concentration among different plant species and tissues (3, 8, 34, 52, 54, 59) (Table 1).

Based on these values, the following concentrations of standards were chosen to represent an undiluted maize leaf extract: nitrate (1×=20 mM KNO$_3$) (Fisher ICN19142805); nitrite (1×=0.03 mM NaNO$_2$)(Sigma S-3421); 19-amino acid cocktail (1×, Table 1). These standards were added to the M9 assay medium in Phase 3, at the dilutions indicated. Each standard was first dissolved in ddH$_2$O and then in 1×M9 medium.

Plant Growth Conditions. *Zea mays* L. (hybrid CG102× CG108) seed was used for all experiments. Seeds were germinated on wet Kimwipes for 3 d then transplanted into individual flat inserts (6×8×5 cm) containing a clay substrate (Turface MVP, Profile Products, USA) and watered with ddH$_2$O only. Growth chamber (Model PGR15, Conviron) conditions were set to 28° C./20° C. (day/night) with a 16 h photoperiod with cool white Supersaver CW/VHO/SS (Sylvania) and enhanced spectrum fluorescent bulbs [(Gro Lite WS GL/WS/VHO (Gro Lite Industrial) and VitaLux Ultra-High Output (Duro-Test)] at 120-150 µmol m$^{-2}$ s$^{-1}$ at pot level. At the 13th day after transplanting, plants were watered with a modified Hoagland's nutrient solution that either contained all nutrients required for growth

TABLE 1

Amino acid concentration of different plant tissues used to determine the composition of the amino acid cocktail.

| 1X AA Cocktail | | | Garden pea | Pinto bean | Chickpea | Kamut | Adzuki bean | Soybean | Pea plant | Maize | Maize | Barley |
|---|---|---|---|---|---|---|---|---|---|---|---|---|
| | | | Pisum sativum L. | Phasedus Vulgaris L. | Cicer arietinum L. | Triticum polonicum L. | Vigna angularis L. | Glycine max | Pisum sativum L. | Zea mays L. | Zea mays L. | Hordeum vulgare |
| | | | seedling axes | seedling axes | seedling axes | seedling axes | seedling axes | Xylem sap | Leaves | Shoot | Leaf aqueous volume | Leaf |
| mM | Supplier number | Amino Acid | mg/g fw | mg/g fw | mg/g fw | mg/g fw | mg/g fw | µmol/ml | nmol/g fw | µmol/g fw | mM | µmol/g fw |
| 10 | Sigma A-3534 | Alanine Ala | 0.4 | 0.3 | 0.3 | 0.75 | 0.5 | 0.04 | 1120 | 6.88 | 1.46 | 1.382 |
| 10 | Sigma A-3784 | Arginine Arg | 0.05 | 0.6 | 0.1 | 0.35 | 1.43 | 0.11 | 270 | | | 0.288 |
| 15 | Sigma A-4159 | Asparagine Asn | 1.95 | 0.6 | 3 | 1.45 | 1.65 | 0.59 | 2510 | 3.56 | 4.77 | 0.08 |
| 10 | Sigma 11189 | Aspartic acid Asp | 0.9 | 0.51 | 0.3 | 0.7 | 0.95 | 0.34 | 1420 | 1.75 | 2.2 | 1.682 |
| 5.02 | Sigma C-7755 | Cysteine Cys | | | | 0.2 | | | | | | |
| 0 | Phyto-Tech G229 | Glutamine Gln | 0.52 | 0.3 | 0.2 | 2.6 | 0.7 | 0.36 | 1710 | 0.24 | 0.1 | 1.738 |
| 10 | Fluka 49449 | Glutamic acid Glu | 0.27 | 0.25 | 0.18 | 0.51 | 0.35 | 0.05 | 780 | 4.96 | 1.47 | 4.573 |
| 5.01 | Sigma G-8790 | Glycine Gly | | | 0.02 | 0.05 | 0.01 | | 300 | 2.98 | 1.42 | 2.393 |
| 5 | Sigma H-8776 | Histidine His | | | 0.45 | 0.35 | | | 60 | | 0.22 | 0.348 |
| 4.75 | Sigma I-7383 | Isoleucine Ile | 0.07 | 0.03 | 0.19 | 0.3 | 0.52 | 0.02 | 60 | 0.06 | 0.12 | 0.074 |
| 4.75 | Sigma L-1512 | Leucine Leu | 0.03 | 0.04 | 0.07 | 0.19 | 0.22 | 0.02 | 320 | 0.1 | 0.1 | 0.102 |
| 11.3 | Sigma L9037 | Lysine Lys | 0.6 | 0.05 | 0.08 | 0.03 | 0.85 | 0.06 | 110 | 0.04 | 0.12 | 0.373 |
| 5.01 | Fluka 64319 | Methionine Met | 0.06 | | | | 0.3 | | 40 | | | |
| 7.99 | Sigma P5482 | Phenylalanine Phe | 0.17 | 0.6 | 0.02 | 0.13 | 0.42 | 0.02 | 40 | 0.06 | 0.08 | 0.112 |
| 5 | Sigma P-4655 | Proline Pro | 0.4 | 0.05 | 0.1 | 2.56 | 0.15 | | | 0.22 | | 0.172 |
| 4.99 | Sigma S4500 | Serine Ser | 0.385 | 0.16 | 0.2 | 0.32 | 0.4 | 0.06 | 270 | 2.35 | 1.57 | 2.023 |
| 15 | Sigma T8441 | Threonine Thr | 0.8 | 0.2 | 0.55 | 1 | 1.2 | | 1080 | 0.25 | 0.35 | 0.731 |
| 2.37 | Sigma T8941 | Tryptophan Trp | 0.18 | 0.03 | 0.12 | 0.03 | 0.18 | | | | | 0.022 |
| 0.26 | Sigma T34754 | Tyrosine Tyr | | 0.01 | 0.05 | 0.02 | 0.15 | 0.01 | | | 0.11 | 0.03 |
| 11.4 | Sigma V0513 | Valine Val | 0.5 | 0.1 | 0.45 | 0.35 | 1.45 | 0.03 | 100 | 0.26 | 0.16 | 0.137 |
| | | Ref | 52 | 52 | 52 | 52 | 52 | 54 | 3 | 34 | 8 | 59 | including nitrogen (+N solution containing 20 mM total N), or all nutrients excluding nitrogen (−N). Both nutrient solutions were at pH 5.7 and contained: 0.1 mM $K_2SO_4$ (Fisher P-304), 1 mM KCl (Sigma P9333), 2 mM $KH_2PO_4$ (Sigma P0662), 1 mM $MgSO_4·7H_2O$ (Sigma 230391) and 0.03 g/liter Plant-Prod Chelated Micronutrient Mix (Plant Products). The +N nutrient solution also contained 6 mM $Ca(NO_3)_2·4H_2O$ (Sigma 237124) and 4 mM $NH_4NO_3$ (Sigma A3795), whereas the −N nutrient solution contained 6 mM $CaCl_2^-$ $2H_2O$ (Sigma C-79). Plants were each watered with a single 20 ml dose of nutrient solution at 40 h before sampling and another 25 ml does at 25 h before sampling. At 17, 10 and 1 h before sampling the excess nutrient solution was poured from each pot and re-watered with 15 ml of fresh nutrient solution per plant. There were 4-5 pots/treatment and the positions of the pots were randomized within a treatment block and changed every other day to minimize positional effects in the growth chamber.

Plant Sampling for GlnLux Versus HPLC Comparisons. At the 15th day after transplanting, leaf tissue was collected at various time points from +N and −N groups, frozen in liquid nitrogen and stored at −80° C. After grinding, each homogenized sample was divided into two, for parallel HPLC and biosensor analysis.

GlnLux Luminometer Measurements of Plant Gln. In the final assay, 1-10 mg of frozen homogenized plant samples were re-ground with silica sand in liquid nitrogen, suspended in 9 μl of $ddH_2O$ (pH 7.0) per mg with 1% final v/v protease inhibitor cocktail (PIC) for plant cell extracts (100% stock, #P9599, Sigma), vortexed, centrifuged for 20 min at 4° C. at 13,000 rpm to remove) tissue debris, and the supernatant was transferred to a new tube placed on ice. The plant extracts were diluted 1000-fold in $ddH_2O$ (pH 7.0) with 1% PIC. Plant extracts were used immediately in luminometer assays.

For luminometer assays, white opaque 96-well reader plates were loaded with 80 μl/well concentrated M9 minimal medium. To each well, 10 μl of the plant extract was added. Finally, a 14 h-Gln-depleted GlnLux culture (pre-depletion $OD_{595}$=0.025) was diluted 10-fold in M9 minimal medium, and 10 μl was added to each well. The 0 μg/ml Gln standard reading was subtracted from all lux values, which were read in randomized replicates of four using luminometer settings as above (see Phase 4).

HPLC Measurements of Plant Gln. Fifteen to two hundred milligrams of weighed frozen homogenized samples were re-ground using a chilled mortar and pestle with silica sand and 0.6-2.0 ml of sulphosalicylic acid (30 mg/ml) (38). The homogenate was centrifuged for 20 min at 16,000×g, the supernatant was collected and the pH adjusted to 7.0 using 4 N NaOH. The sample was stored at −20° C. for up to 24 h. For HPLC analysis, the amino acid samples were separated by reverse-phase HPLC following automatic derivatization with o-phthalaldehyde (1) using an Agilent Model 1100 series HPLC [Agilent Technologies Inc. (Mississauga, Canada) equipped with a degasser, binary pump, autosampler, temperature-controlled column holder, and fluorescence detector].

Statistical Analysis. To test for the linearity of the biosensor response, linear regression analysis was performed using a Goodness of Fit ($R^2$) test. To test for biosensor sensitivity, the slope (m) of the biosensor response (RLU) was measured between 0 μg/ml Gln and a low Gln standard as noted; the biosensor was deemed to be sensitive to the low Gln standard if the slope value was significantly different from zero (P=0.05). HPLC versus GlnLux correlation analysis was performed using the Spearman rank test for non-parametric data. All statistical analyses were performed using InStat Prism Software (v5, GraphPad Software, USA).

Results

Figure 8:
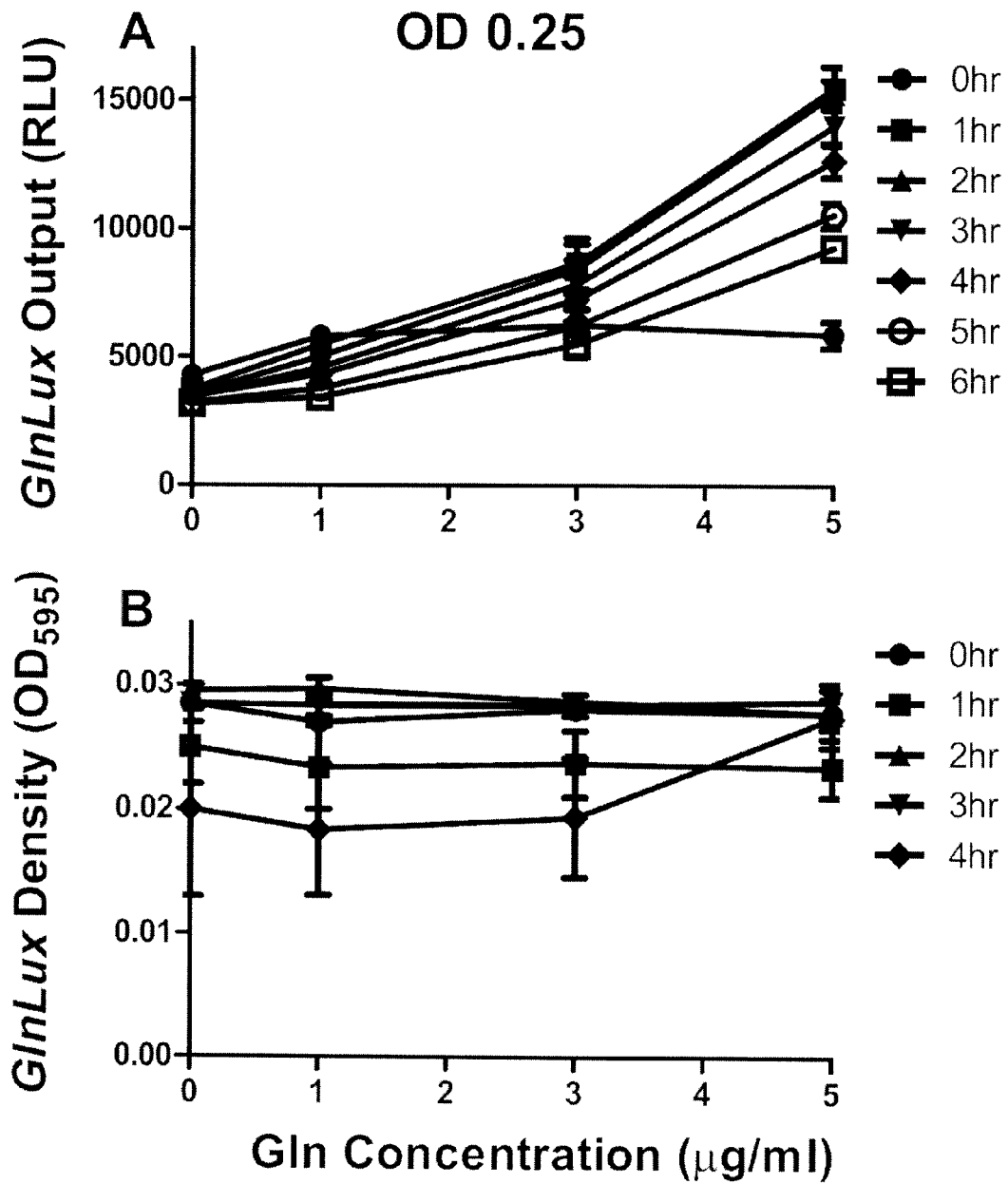
FIGS. 8A and 8B are graphs comparing GlnLux culture responses to exogenous Gln using (FIG. 8A) lux output compared to (FIG. 8B) $OD_{595}$ quantification, at different times following Gln exposure. For lux quantification, GlnLux cells were diluted to $OD_{595}$ 0.25 at the onset of Phase 2, and then incubated in Gln-free M9 minimal medium for 14 h to deplete endogenous free Gln, prior to incubation with Gln standards (Phase 3) and lux quantification (Phase 4, 1-s luminometer reads).

Lux Versus Optical Density. The $Kan^R$ E. coli strain auxotrophic for Gln (2) failed to grow in M9 minimal medium but grew in M9 medium supplemented with Gln (overnight $OD_{595}$=0.0003 without Gln versus 0.1417 with 0.1462 g/liter Gln and 0.345 with 1.462 g/liter Gln). The strain was transformed with the $Ap^R$-resistant plasmid pT7-lux (37) containing a constitutive promoter driving the luxCDABE operon to create strain GlnLux. Overnight cultures were grown to $OD_{595}$=0.3 in LB medium to permit growth (Phase I), then resuspended and grown for 14 h in M9 minimal medium lacking Gln to deplete endogenous free Gln (Phase 2). GlnLux cells were then incubated with different concentrations of Gln in deep well plates (Phase 3), and samples taken hourly for measurements of $OD_{595}$ and lux in shallow plates (Phase 4). The results showed that luminescence, but not the $OD_{595}$,. changed proportionately to increasing Gln (FIG. 8). Thus, the luxCDABE strain (GlnLux) was used for all further experiments.

Pre-Assay Modification for Improved Sensitivity. To improve luminometer-based quantification of Gln using GlnLux, GlnLux cultures were diluted prior to the assay; the goal was to reduce background noise and increase the amount of exogenous Gln available per GlnLux cell thus improving assay sensitivity. As GlnLux cultures were diluted, the background noise decreased (FIG. 2A-F). Assay sensitivity was quantified by measuring the slope (m) of the GlnLux response at zero Gln versus low concentrations of Gln. The greatest assay sensitivity occurred at the $1/10^{th}$ and $1/100^{th}$ dilutions of $OD_{595}$=0.025 GlnLux, allowing ≥0.001 μg/ml (6.8 nM) of Gln to be detected (FIG. 2E,F). For all further experiments, only the $1/10^{th}$ dilution was used since it required a shorter incubation time with Gln to achieve a linear response (FIG. 2E, 2F and FIG. 9). When using the $1/10^{th}$ dilution, a 14 h pre-incubation in M9 minimal medium was confirmed to be a desired duration to deplete endogenous Gln from GlnLux cells (Phase 2), though incubations ranging from 7-24 h were beneficial (data not shown).

Luminometer Assay Linearity. The linearity of the luminometer assay was improved by incubating exogenous Gln with GlnLux cells for different incubation times (Phase 3). Using the above culture dilution, GlnLux output was observed to peak at 0.1-0.5 μg/ml Gln (FIG. 3A). An incubation time of 3 h maximized linearity (Goodness of Fit $R^2$=0.91); the linear concentration range of the assay extended across three orders of magnitude from 0.0001-0.1 μg/ml Gln (FIG. 3B-3I). Assay linearity was found to be robust against shorter and longer incubations (2-4 h: $R^2$=0.88-0.91) (FIG. 3B-3I), while an extended incubation time (7 h) shifted the linear range of the assay 10-fold to 1 μg/ml (FIG. 9J).

Luminometer Assay Efficiency. The efficiency of the luminometer assay was improved: rather than switching from deep-well plates to 96-shallow-well plates, it was determined that sample incubations (Phase 3) and luminometer readings (Phase 4) could both be performed in the same shallow plates without altering lux output (data not shown). This improvement reduced the need for hourly aliquoting.

Figure 3:
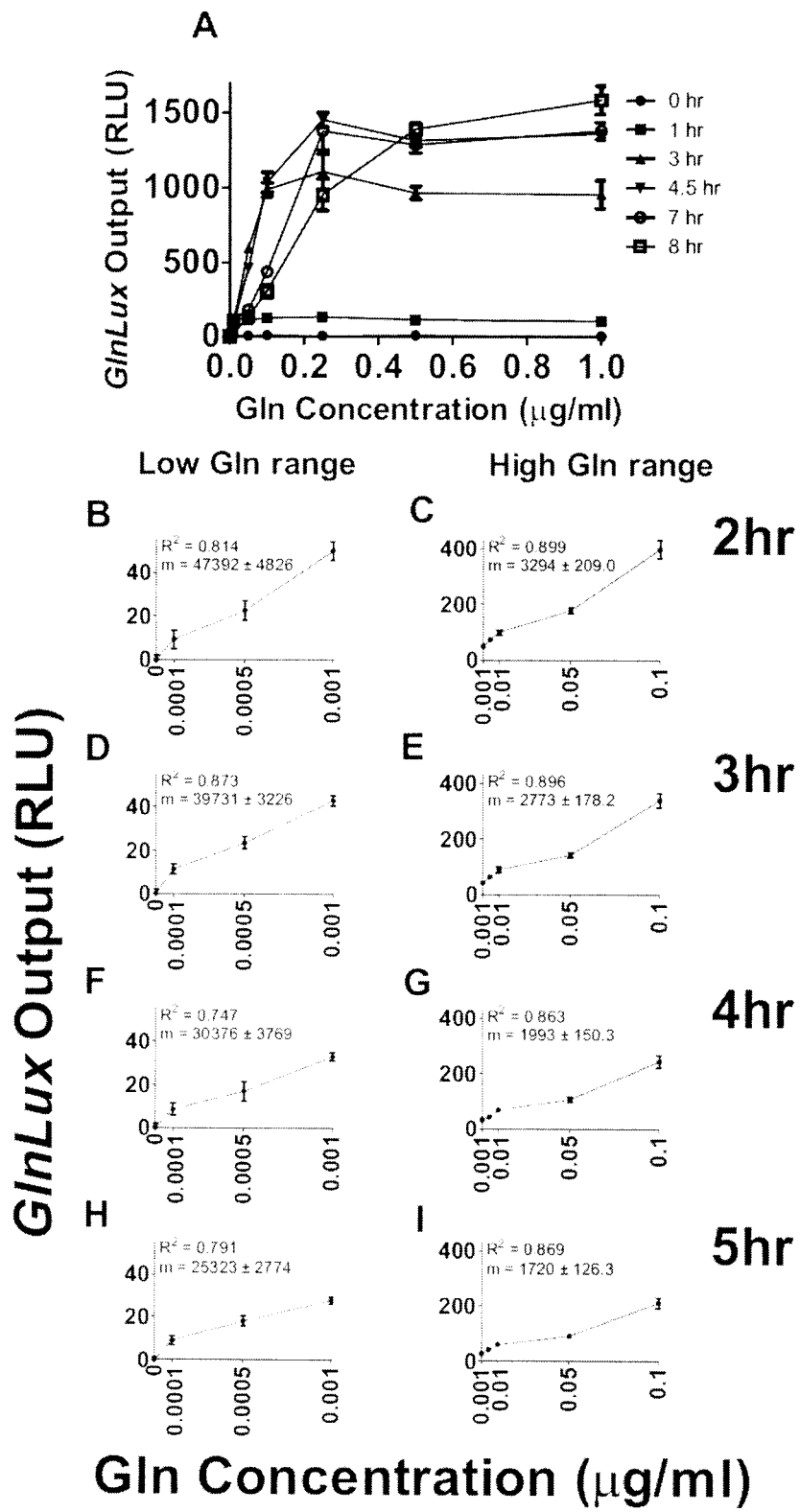
FIG. 3A to 3I show graphs representing the effect of incubating GlnLux cells with Gln for different durations on luminometer assay linearity (Phase 3).
Figure 12:
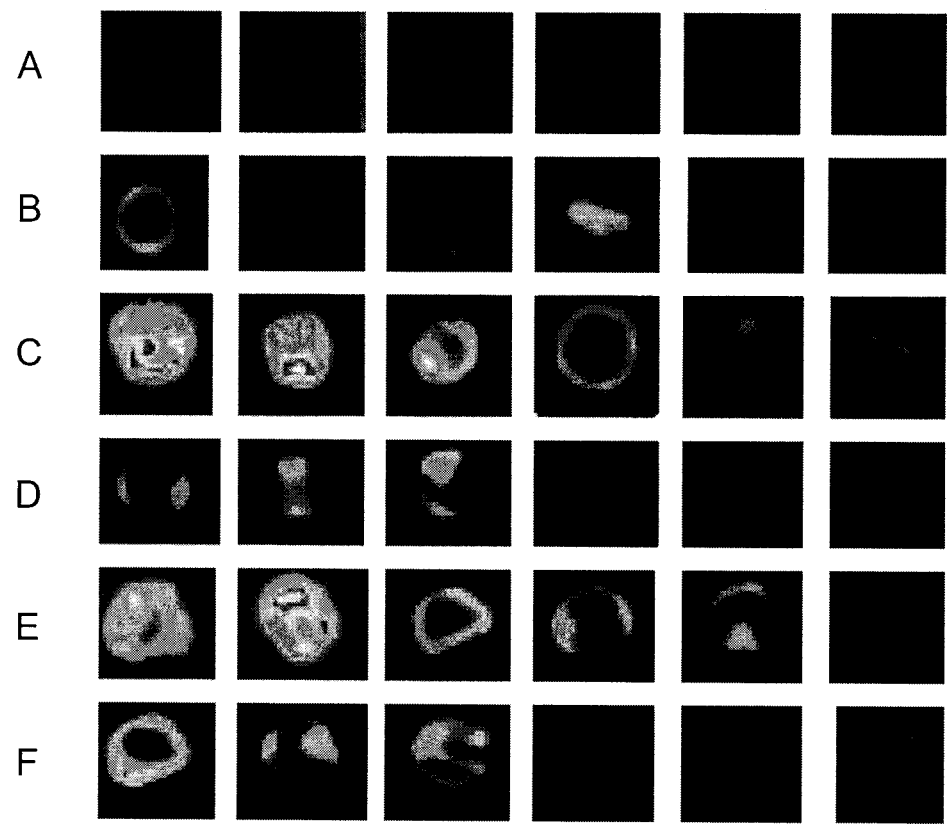

GlnLux Specificity. An anticipated challenge of using GlnLux to quantify Gln in tissue extracts, including plants, was the presence of other nitrogenous compounds that might interfere with the assay. The specificity of GlnLux to Gln was tested. Nitrite, nitrate and 19 other amino acids were added into the assay medium (Phase 3) at concentrations equivalent to 1/100-1/10,000 of their expected concentrations in plants. These dilutions were chosen as we calculated that 1/1000 dilution of a plant extract would be in the linear range of the GlnLux assay (FIGS. 2, 3 and 12). Neither diluted nitrite, nitrate nor a cocktail of 19 amino acids, had any significant effect on GlnLux output (Kruskall-Wallis Tests: nitrite:

p=0.97-1.0; nitrate: p=0.92-0.95; amino acids: p=0.57-0.76) (FIG. 4). It was unnecessary to test ammonium as it was already present at a high concentration in M9 minimal medium; M9 alone did not elicit significant GlnLux expression (see 0 µg/ml Gln, FIG. 2F).

Luminometer Assay Robustness. There was concern that endogenous proteases in plant extracts would cause protein breakdown during the extended incubation of extracts with GlnLux cells, leading to sporadic increases in free Gln levels. We tested the effect of adding a protease inhibitor cocktail (PIC) designed for plant cell extracts to either the plant tissue extraction buffer (EB+), the incubation buffer (IB+, Phase 3) or both (Table 2). Improved correlation between measurements of plant extracts using GlnLux versus HPLC was used to indicate improved robustness of the biosensor assay. PIC addition to both the extraction and incubation buffers improved the robustness of the GlnLux assay dramatically (Spearman r increased from 0.1 to 0.9) but caused lux output to decline by >99% (measured by lux output slope, m) (Table 2). When PIC was added to the extraction buffer alone, assay robustness improved (r=0.7) without dramatic losses in GlnLux output (Table 2). The negative impact of PIC in the incubation buffer was due to its direct inhibitory effect on GlnLux cells as shown by addition of PIC to an extract-free assay containing only Gln standards (Table 2). PIC was added into the extraction buffer only for all subsequent experiments.

Example 2

Preparation of GlnLux-Agar

This example shows a mode of preparation of GlnLux-agar. For the purposes of the present invention, GlnLux-agar is a medium for culturing, screening or selecting nitrogen-fixing microbes or inoculant nitrogen-fixing microbes. It is also a medium which can be used for quantification of nitrogen and visualization of free glutamine in plant organs.

Preparation of GlnLux-Agar and Imaging Using a Photon Capture Camera. GlnLux bacteria were prepared by growth at 37° C. with shaking at 250 rpm overnight in 200 ml LB in a 500 ml flask, supplemented with 400 µl of 2.0 M glucose and 200 µl of each of 50 mg/ml kanamycin, 100 mg/ml carbenicillin and 0.2 M Gln. After overnight growth (16 h) the culture was spun down at 1100×g at 25° C. for 10-20 min. The supernatant was decanted and the culture was washed 3× in 0.01 M potassium phosphate buffer (pH 7.0) with centrifugation as above. Finally, the culture was resuspended in sterile M9 minimal medium to $OD_{595}$=1.0.

For agar plates or slabs, following improvement (see Results), concentrated M9 minimal medium prepared from sterile stock solutions was mixed with autoclaved molten bacto-agar (10 g/liter final concentration), cooled, supplemented with sterilized casamino acid solution (5 g/liter final

TABLE 2

Effect of protease inhibitor cocktail (PIC) on the linearity and signal of the GlnLux assay.

| | | Plant Extracts * | | | | | Gln Standards 0-0.05 | | |
|---|---|---|---|---|---|---|---|---|---|
| | | EB−/IB− | EB+/IB− | EB−/IB+ | EB+/IB+ | | EB−/IB− | EB+/IB− | EB−/IB+ | EB+/IB+ |
| 3 hr | Slope (m) | 137779 | 39415 | 6063 | 6322 | Slope (m) | 2080 | 3940 | 316.6 | 351.4 |
| | Spearman r | 0.1 | 0.7 | 0.9 | 0.9 | Spearman r | 1 | 0.9 | 1 | 1 |
| 5 hr | Slope (m) | 912156 | 204150 | 5096 | 8047 | Slope (m) | 1736 | 2013 | 82.74 | 97.93 |
| | Spearman r | 0.1 | 0.6 | 0.7 | 0.9 | Spearman r | 1 | 0.9 | 0.9 | 1 |
| 7 hr | Slope (m) | 366033 | 163217 | 2164 | 3123 | Slope (m) | 928.3 | 1160 | 44.22 | 71.06 |
| | Spearman r | 0.1 | 0.3 | 0.7 | 0.9 | Spearman r | 1 | 0.9 | 0.7 | 1 |
| 9 hr | Slope (m) | 242943 | 96215 | 1629 | 2453 | Slope (m) | 747.3 | 869.3 | 57.93 | 41.89 |
| | Spearman r | 0.1 | 0.3 | 0.7 | 0.9 | Spearman r | 1 | 0.9 | 0.7906 | 1 |

*n = 5
Protease inhibitors were added in either the plant tissue extraction buffer (EB) or later in the incubation buffer (IB) (Phase 3)

Figure 5:
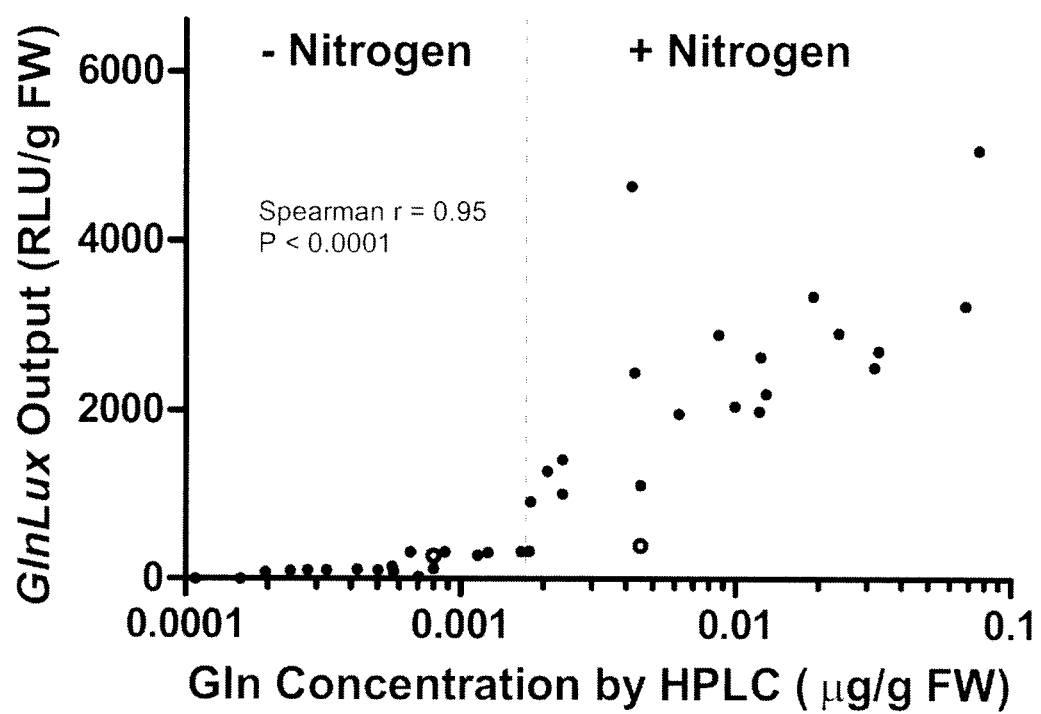
FIG. 5 shows the validation of the GlnLux luminometer assay to quantify free Gln in plant tissue extracts by comparison to standard HPLC. Leaf extracts of maize seedlings previously treated with fertilizer solution +/− nitrogen, were quantified using HPLC, and independently tested using the GlnLux luminometer assay, the latter using 1/1000 dilutions of maize extract. Each value is an extract from one leaf of one seedling. The coefficient of correlation (Spearman r) between GlnLux and HPLC assays is indicated. HPLC and GlnLux readings segregated based on the prior nitrogen fertilizer treatment (vertical dotted line) with the exception of two outliers noted (open circles). GlnLux measurements were generated using the following conditions: 1/10 $OD_{595}$ 0.025 culture dilution (Phase 2), 14 h depletion of endogenous Gln in M9 minimal medium (Phase 2), 4 h sample incubation (Phase 3), 1-s read time (Phase 4).

Luminometer Assay Validation. The accuracy of the modified GlnLux luminometer assay for quantifying Gln in plant tissue extracts was determined by comparison to standard HPLC (1). Using split tissue extracts from maize seedlings, an excellent correlation was found between measurements made using GlnLux compared to HPLC [Spearman r=0.95, with no outliers removed (p<0.0001, d.f.=39)] (FIG. 5). The seedlings had been exposed to fertilizer solution with or without ammonium/nitrate which was expected to be assimilated into Gln and transported to leaves (40). GlnLux measurements of leaves could distinguish plants that had been fertilized with ammonium/nitrate or not (FIG. 5).

The final GlnLux assay required only small amounts of biological material (1 mg of leaf tissue, diluted a further 1000-fold), used only buffered water for the tissue extract, and required only a 1-s read time in the luminometer. The GlnLux luminometer assay is thus a highly sensitive and accurate tool for quantifying biologically relevant concentrations of Gln in plant tissue extracts.

concentration), further cooled to 42° C., and mixed with 10% (v/v) of the $OD_{595}$=1.0 GlnLux culture before pouring. This is referred to as M9 GlnLux-agar.

For all lux imaging, a ChemiProHT Luminescence Imaging System (Roper, USA) was used with Winview 32 software (10). Dark noise was reduced by pre-chilling the CCD chip to −80° C. (11).

In the final, modified plant imaging protocol, maize seedling tissues were frozen in liquid nitrogen and thawed at room temperature for 30 s. Roots and adaxial leaf surfaces were placed in contact with room temperature M9 GlnLuxagar. Tissues were pressed down. Plates were inverted, imaged at the zero time point, then placed at 37° C. for 1-6 h with hourly imaging with 200-600 s exposure times.

Example 3

Modification of GlnLux-Agar for Direct Imaging of Gln in Plant Organs or Tissues GlnLux-agar was used to visualize Gln directly in intact plant tissues. Gln is the final product of absorbed, assimilated, and translocated nitrogen in plants and therefore is useful as a proxy for detecting bioavailable soil nitrogen, efficient nitrogen uptake by roots, assimilation of nitrogen into amino acids and translocation to appropriate plant organs. To perform the modifications, with the goal of improving the features of the glutamine biosensor, cellulose paper filters containing pure Gln were placed on top of GlnLux-agar and then visualized using a CCD camera.

To reduce background noise from GlnLux-agar, an attempt was made to reduce endogenous Gln in GlnLux cells by pre-incubating them in M9 minimal medium agar (containing 10% v/v $OD_{595}$=1.0 GlnLux) for 14 h prior to adding the Gln-filter standards. Surprisingly, this treatment resulted in higher background and was not used further (FIG. 6A, B). To improve lux signal, increasing densities (10-50% v/v) of the bacterial culture in the GlnLux-agar were tested: higher densities increased signal output but also background noise (FIG. 6C-E); thus, the original 10% v/v cell density was used for all subsequent experiments. To boost GlnLux metabolism and thus signal, increasing concentrations (0-2%) of casamino acids were added into M9 GlnLux-agar using the 10% (v/v) cell density. The addition of casamino acids improved both sensitivity and signal (FIGS. 6F-I); 0.5% casamino acids was chosen for further experiments. Finally, to improve signal strength, the effect of increasing the incubation time of Gln-Lux-agar with Gln standards at 37° C. prior to imaging, was tested (at 10% v/v density, and 0.5% casamino acids). A 2-3 h pre-incubation gave the highest signal:noise ratio (FIGS. 6J-L) and was used for all subsequent experiments. The modified GlnLux-agar imaging assay achieved a sensitivity of 0.00001-0.0001 M Gln.

Pre-Treatments Required for Imaging Gln in Intact Plants. To further modify the GlnLux-agar imaging assay, we attempted to increase Gln leakage from plant tissues. Freeze-thawing maize seedlings prior to their placement on GlnLux-agar was required for imaging (FIG. 10A) compared to the room-temperature control (FIG. 10B). Maize seedling tissues were frozen in liquid nitrogen and thawed at room temperature for 30 s. Mechanical abrasion before freeze-thawing reduced the spatial resolution of the signal and was not used further (FIG. 10A, 10B). Roots and adaxial leaf surfaces were placed in contact with room temperature M9 GlnLux-agar. Tissues were pressed down. Plates were inverted, imaged at the zero time point, then placed at 37° C. for 1-6 h with hourly imaging with 200-600 s exposure times. No difference was found in the lux signal when maize root tissues were laid on the GlnLux-agar surface compared to embedding plant tissue within GlnLux-agar (FIG. 10C, 10D).

Imaging of Fertilized Versus Unfertilized Plant Tissues Using GlnLux-Agar. As noted earlier, nitrogen soil fertilizers (e.g. nitrate, ammonium) are taken up by plant roots, and assimilated into Gln and other amino acids (40). We used CCD imaging of freeze-thawed plant tissues on GlnLux-agar to distinguish fertilized from unfertilized roots (FIG. 7A-H). For root imaging (FIG. 7A, B), plants were germinated and grown in vertical germination bags (16×16 cm) to allow roots to grow flat for easier lux imaging. The seedlings were treated with ddH$_2$O only for 14 d using the above growth chamber conditions. At 14 h before sampling, the plants were watered with a single dose of 10 mM $NO_3$ or water.

Two-week old seedlings were fed with nitrate once, 14 h prior to freeze/thawing. In the absence of nitrate feeding, the signal from GlnLux biosensor cells adjacent to roots was low (FIG. 7A), whereas with nitrate feeding, a large increase in lux signal was observed (FIG. 7B). Leaves were also imaged after feeding their roots with fertilizer solution with or without ammonium/nitrate five times between ~50 to ~10 h prior to freeze/thawing. GlnLux-agar exposed to leaves from nitrogen-deficient seedlings emitted a low signal (FIGS. 7C-E), whereas there was a dramatic increase in lux emission from nitrogen-treated seedlings (FIGS. 7F-H). This demonstrates that GlnLux-agar may be used as an above-ground visual test for below-ground nitrogen fertilization.

The Spatial Resolution of the GlnLux-Agar Imaging Assay. Apart from nitrogen uptake from the soil, nitrogen is also internally scavenged from a senescing leaf via protein degradation and then re-assimilated into Gln at the base of the leaf from where it is exported to growing organs via the vascular tissues (20). In previous studies using maize leaf, Gln levels were shown to be highest in the base of the leaf, decreasing by 50% in the middle and by >90% in the most apical two-fifths of the leaf towards the tip (8). This is consistent with recent studies showing highest accumulation of glutamine synthetase mRNA and protein at the base of leaf 3 in maize seedlings (30, 35). Consistent with this spatial pattern, in fertilized leaves, the highest lux expression in Gln-Lux-agar was consistently at the base to middle zones along the midvein, which contains a large quantity of vascular tissues, and lowest at the tip (FIG. 7I). This result suggests that GlnLux-agar can resolve spatial differences in plant Gln concentrations.

Therefore, GlnLux-agar may be a useful indicator of total plant free nitrogen status (inorganic and organic fractions) rather than Gln alone. It may be used to select plant genotypes with improved nitrogen uptake from soil, improved assimilation into amino acids and/or improved scavenging of nitrogen from senescing plant cells. One desirable use of GlnLux would be for plus/minus type assays, when the plant tissue extract can be diluted up to about 1000-fold and when total plant nitrogen status is of interest.

Example 4

Figure 11:
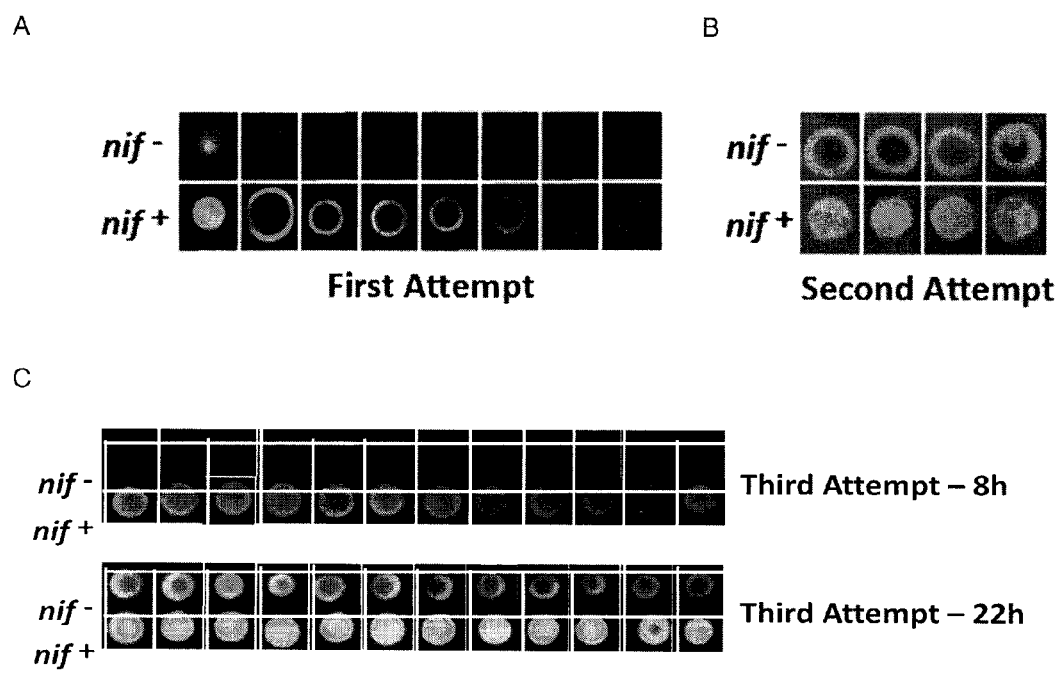

GlnLux-Agar for Culturing, Screening or Selecting Nitrogen-Fixing Bacteria or Inoculant Nitrogen-Fixing Bacteria FIGS. 11 A, B and C show a first (FIG. 11A), second (FIG. 11B) and third (FIG. 11C) attempt in imaging *Bradyrhizobium japonicum* wild-type nitrogen fixing strain 110 (nif+), and mutant strain 510 (nif−) which is deficient in fixing nitrogen, in GlnLux-agar. It is known that the nif genes are genes encoding enzymes involved in the fixation of atmospheric nitrogen. *B. japonicum* colonies were incubated on GlnLux-agar for 18-20 h. The photon capture CCD images shown used 10 minute exposure times. This experiment demonstrates that GlnLux-agar can be used to culture, screen and select for nitrogen fixing microbes.

When designing an inoculant, the selection of nitrogen-fixing microbes, such as bacteria, becomes very important. The GlnLux-agar is a novel medium for culturing, screening or selecting nitrogen fixing microbes to be used as inoculants in a simple and inexpensive manner.

Figure 6:
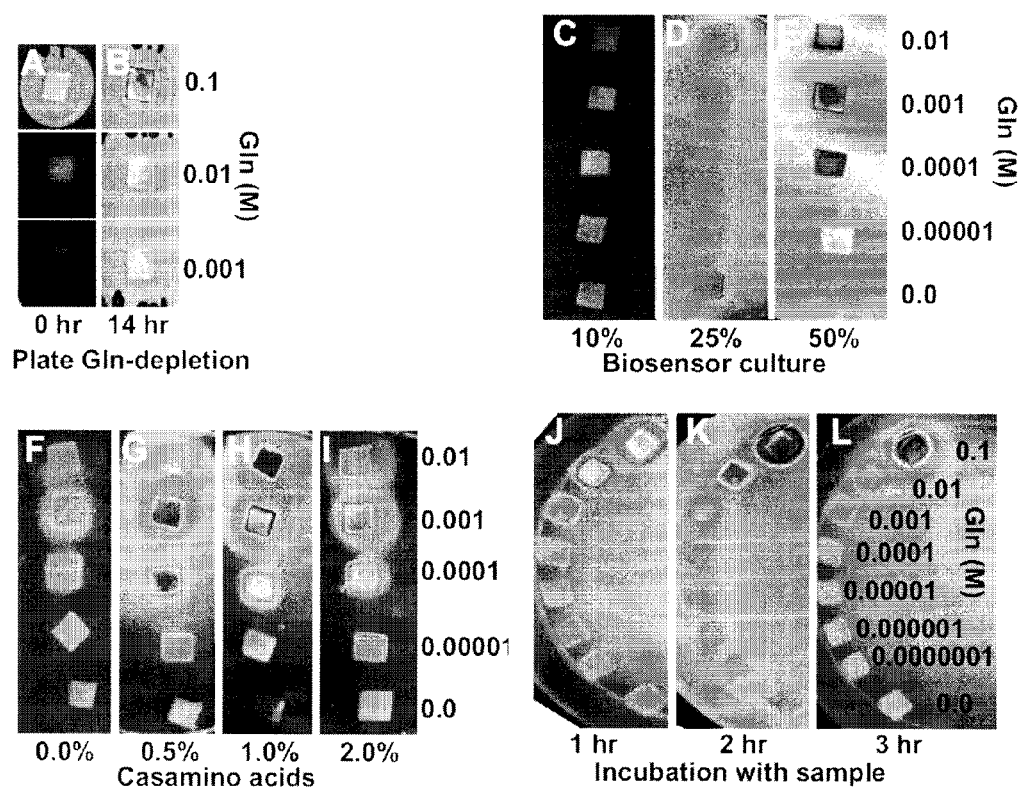
FIG. 6A to 6L provide visual screening of Gln in vivo using a photon capture camera thereby enabling improvement of the GlnLux-agar (or culture medium of the present invention). Filter papers supplemented with different concentrations of Gln were placed on M9-agar containing GlnLux cells; the opposite agar surface was then imaged using a photon capture CCD (or charge-coupled device) camera (600 s exposure). Shown is the step-by-step modification.
Figure 7:
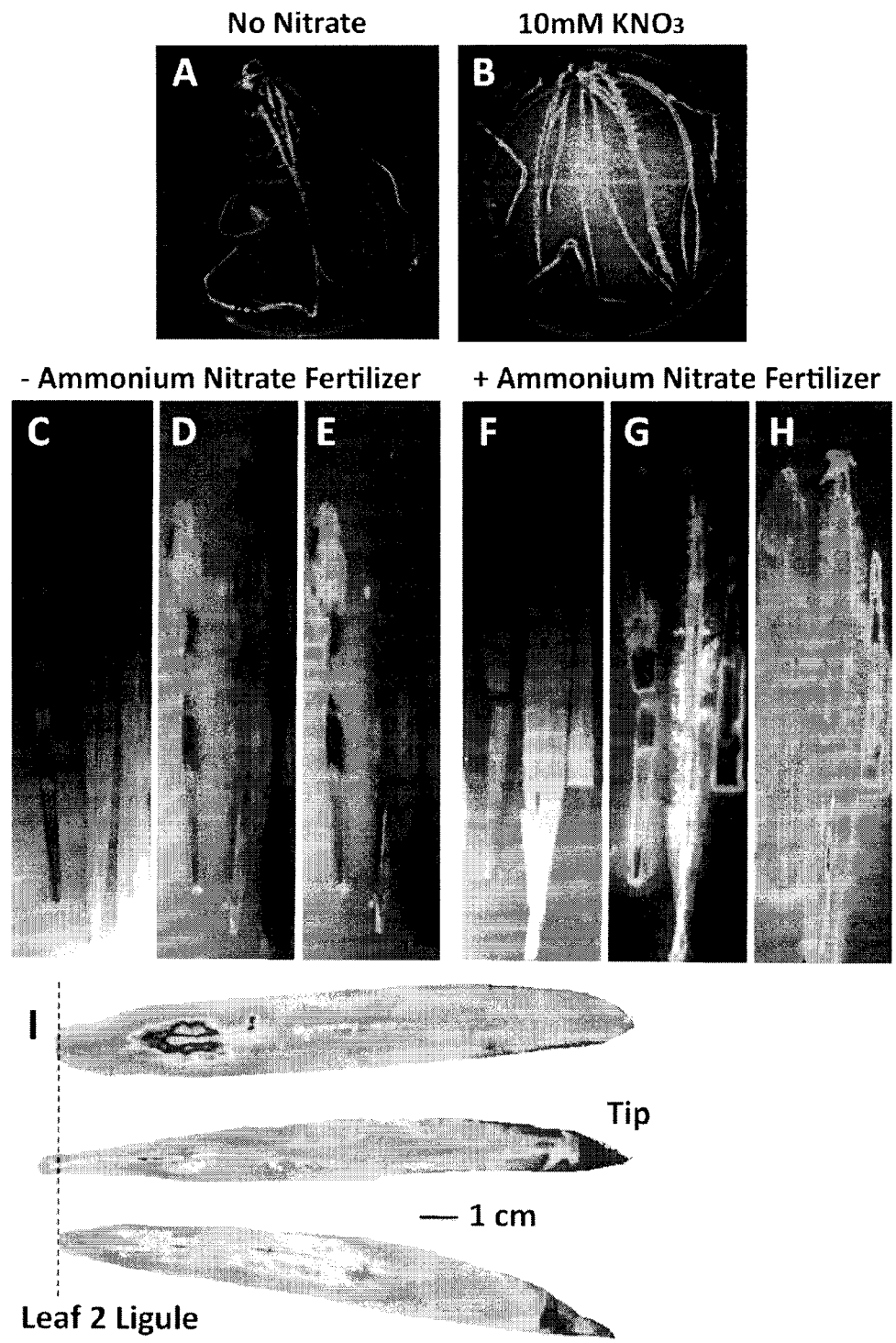
FIG. 7A to 7I show the luminescence in vivo imaging of Gln in plant organs using GlnLux-agar.

GlnLux is a novel tool for plant scientists and the agriculture industry. Levels of free Gln are an early indicator of whether a plant is receiving sufficient nitrogen fertilizer for optimal growth (46). Specifically, the concentration of shoot Gln indicates the availability of nitrogen around roots as well as a plant's ability to uptake, biochemically assimilate and appropriately transport nitrogen (22). The GlnLux luminometer assay described herein was able to quantify Gln in plant tissue extracts using a rapid aqueous extraction procedure from as little as 1 mg of tissue. GlnLux output was found to highly correlate with traditional HPLC-based quantification of Gln in plant tissue extracts (FIG. 5). Furthermore, GlnLux embedded in agar (GlnLux-agar) permitted CCD imaging of Gln in intact plant organs (FIG. 7), at a sensitivity threshold of 0.01-0.1 mM Gln (FIG. 6). Both assays were sufficient to distinguish whether or not seedlings had been fertilized with nitrogen (FIGS. 5, 7). Furthermore, spatial imaging of mature leaves using GlnLux-agar suggested that the highest Gln concentration was at the leaf base, in the midvein region (FIG. 7I), consistent with Gln being scavenged for export to growing organs (metabolic sinks), and in agreement with both spatial HPLC analysis (8) and expression of Glutamine Synthetase mRNA and protein (30, 35).

One possible concern was that the increase in GlnLux-agar signal from nitrogen-fertilized plant organs (FIG. 7) was not due to Gln but due to elevated levels of tissue nitrate and other amino acids, which accumulate following fertilization (13, 31). However, in stem and leaf xylem sap, nitrate levels have been shown to range from 1-6 mM in maize (31, 45), and up to 20 mM in wheat following nitrate treatment (28). The maize extracts used in the luminometer assay were diluted 1000-fold (FIG. 5), and hence contained extremely low nitrate concentrations that would not be expected to significantly affect GlnLux output (FIG. 4).

A particularly desirable use for the GlnLux-agar is as an indicator of total plant free nitrogen status (inorganic and organic fractions) rather than Gln alone. Another use of Gln-Lux would be for plus/minus type assays, when the plant tissue extract can be diluted 1000-fold and when total plant nitrogen status is of interest. Future applications of GlnLux may be to indicate nitrogen fertilizer uptake and ability to produce high-protein grain, as both have been shown to correlate with total plant nitrogen status (5, 9, 44, 62). Placement of leaf discs on GlnLux agar could be used in non-destructive, high throughput assays for real time detection of root nitrogen uptake, assimilation, transport and remobilization (22, 39) and as an inexpensive tool to facilitate crop breeding and production.

Example 5

Engineering and Testing of a Glutamine Biosensor for Soil Nitrogen

Growers such as corn farmers want to know whether or not to "top up" fertilizer (sidedress) in the initial weeks after planting. Current early-season diagnostic tests of available soil nitrogen have been ineffective. The efficacy of the GlnLux technology described herein was tested for this purpose, specifically visualizing leaf-punches for Gln to measure how much nitrogen is actually being taken up by corn plants. This represents a novel approach to the problem compared to traditional testing of soil directly which has proven ineffective.

Methods:

The GlnLux technology of Example 3 was tested under real-world conditions in a farmer's field. In a blind experiment, different rates of nitrogen were applied in cornfields near Woodstock, ON, as shown in Table 3. Soil nitrogen measurements were subsequently taken. Expanding rib 5 midrib leaf punches (1 cm diameter) were taken in six replicates from two-week-old corn seedlings (V6 tip stage) growing in the field (and also at later stages). The leaf punches were frozen and taken to the lab where they were exposed to the GlnLux biosensor technology for 10 minutes.

TABLE 3

| | Nitrogen application rate (lbs/acre). | | | |
|---|---|---|---|---|
| Treatment | Pre-plant 1 (2 weeks pre-planting) | Pre-plant 2 (1-5 days pre-planting) | Post-plant (1-2 weeks post-planting) | Total nitrogen |
| A - Low | 35 | 0 | 0 | 35 |
| B - Medium | 35 | 45 | 0 | 80 |
| C - High | 35 | 95 | 0 | 130 |
| D - High | 35 | 95 | 60 | 190 |
| E - High | 35 | 155 | 0 | 190 |
| F - High | 35 | 0 | 155 | 190 |

Results:

FIG. 12 shows that the GlnLux technology was able to distinguish between low (35 lbs/acre), medium (80 lbs/acre) and high (≥130 lbs/acre) levels of soil nitrogen, though some variation was observed between replicate plants (6 shown per N treatment). Existing commercial technologies that claim to distinguish bioavailable N (i.e. GreenSeeker, SPAD meters) could not distinguish between any of these application rates. Therefore, GlnLux is a promising technology for measurements of early season soil N. The glutamine biosensor described herein thus could be used as a mail-in technology for farmers into soil-testing labs.

The data shown in FIG. 12 also provides evidence for other applications of the glutamine biosensor. For example, Gln-Lux could be used to screen commercial soil amendments, fertilizer formulations, green manures or soil inoculants for improved soil nitrogen availability or uptake. Additionally, GlnLux could be used by large breeding companies (e.g. Pioneer) to screen corn, cereals, and all other crops for alleles or transgenes that improve nitrogen uptake from soil and subsequent assimilation into amino acids.

Example 6

Use of the Glutamine Biosensor as a Rapid Visual Diagnostic Technology for Directly Determining Microbial Nitrogen Fixation Legumes such as soybeans associate with microbial strains such as *Rhizobia* bacteria, which convert atmospheric gas into nitrogen fertilizer, a process called biological nitrogen fixation. There exist no high-throughput methods to quantify biological nitrogen fixation directly from microbial colonies on agar plates. Such a technology could be used for high-throughput diagnostic screening to (561) detect novel nitrogen fixing strains, such as *Rhizobia* strains, from soil; or (2) improve commercial nitrogen fixing (e.g. *Rhizobium*) inoculants (using, e.g., mutagenesis, directed evolution or long-term rounds of selection) for improved efficiency of biological nitrogen fixation including under stress conditions (e.g. when farmers add nitrogen fertilizer to soil which represses biological nitrogen fixation; under low pH; low/high temperature, salt, etc.).

Three independent tests have now validated the use of the glutamine biosensor as a rapid visual, diagnostic technology of biological nitrogen fixation directly using bacterial colonies growing on the GlnLux-containing agar of Example 3 or variations thereof that supported growth of the relevant Rhizobial strains. First, wild-type stains of *Rhizobia* (nif+) were compared to mutant strains (nif−) defective for the gene responsible for making nitrogen fertilizer [nitrogen fixation (nif) gene, encoding nitrogenase]. As is shown in FIG. 13, GlnLux-containing agar media effectively distinguished wild-type from mutant bacterial colonies (12 replicates shown per strain). Two independent bacterial species gave similar results: *Bradyrhizobium japonicum* USDA510/110 which fixes nitrogen in soybeans and other legumes; and *Sinorhizobium meliloti* Rm1312/J0810 which fixes nitrogen in alfalfa, indicating that the glutamine biosensor is effective across species.

The existing acetylene reduction test requires days of initial bacterial growth, and requires gas from the bacteria to be collected and analyzed (using a gas chromatography machine). What is particularly remarkable of the data shown in FIG. 13 is that by using the glutamine biosensor described herein, microbial colonies can be tested directly, and after a short growth period (e.g., only about 8-22 h) using a 10 minute long test. This technology therefore opens the door to testing thousands of microbes per day, at a remarkable time and cost savings.

Two other validations of the biological nitrogen fixation detection technology were also performed. A library of 90 bacteria, of which a subset tested positive for biological nitrogen fixation using the glutamine biosensor of Example 3, was independently tested (FIG. 14A). The results were then correlated to other approaches. In the first test, since only those bacteria capable of biological nitrogen fixation contain the nif genes, DNA analysis was used (Southern dot blot using nifH probe) to determine which bacteria contain nif genes (FIG. 14B). In the second test, the traditional acetylene reduction assay was used. Of 55 bacteria that tested positive for biological nitrogen fixation using the glutamine biosensor, 54 were positive using these traditional tests, a 98% match, suggesting a false positive rate of ≤2% and a false negative rate of ≤9%. The single strain that was negative for the dot blot and acetylene reduction assay had a GlnLux score of 1 (low positive) indicating that a slight smudge or stain may have caused the GlnLux result to be mis-read as a positive signal. It is noted that, in comparing the DNA method to the acetylene reduction assay method only a 79% correlation was observed, suggesting the problem may lie in the traditional tests, not in the glutamine biosensor described herein.

Example 7

Quantification of Nitrogen Fixation

A further biological nitrogen fixation diagnostic application of the glutamine biosensor involves the use of luminescent plate readers. This represents a more quantitative technology than the use of a CCD camera-based visualization approach that has been described above. In this example, Rhizobial cells were co-incubated with GlnLux. Secreted Gln (and possibly other amino acids) from the Rhizobial cells stimulated GlnLux which then emitted photons that were quantified using a plate reader luminometer. To validate this application, *Rhizobium* cells were given treatments known to either stimulate or repress nitrogen fixation prior to co-incubation with GlnLux. First, Rhizobial cells were treated with amino acids (casamino acids) to stimulate nitrogen fixation. As is shown in FIG. 15A, the addition of casamino acids dramatically increased GlnLux output (see −N+C column). However, the addition of casamino acids would also increase Gln levels in *Rhizobium* cells, which would subsequently elicit GlnLux upon co-incubation. To distinguish the effect of added casamino acids on biological nitrogen fixation from this artifact, casamino acids were added to both a wild-type *Rhizobium* strain (strain 110) and a nitrogenase mutant derivation incapable of nitrogen fixation (strain 510); the resulting lux outputs from GlnLux following separate co-incubations were then subtracted (wild-type minus mutant) to calculate the effect of casamino acids on biological nitrogen fixation (FIG. 15B). The calculation shows that casamino acids stimulate biological nitrogen fixation. Furthermore, ammonium (N) is known to repress biological nitrogen fixation, a dramatic effect called "ammonium shut-off". As shown in FIG. 15B, when ammonium was added to Rhizobial cells (along with casamino acids, +N+C column), it reduced the elicitation of GlnLux output compared to the control (−N+C column). Similarly, when Gln was added instead of all 20 amino acids (in casamino acids), it also repressed nitrogen fixation as predicted (FIG. 15B).

For further validation, Rhizobial cells were incubated either in the presence of oxygen or anaerobically. Oxygen is a strong inhibitor of biological nitrogen fixation, while anaerobic conditions stimulate biological nitrogen fixation. As is shown in FIG. 15C, the GlnLux biosensor was able to quantify the effect of oxygen on biological nitrogen fixation in Rhizobial cells using a plate reader. Furthermore, GlnLux could quantitatively distinguish between the triple treatments of oxygen, casamino acids and ammonium (FIG. 15C). This data validates the use of GlnLux for the quantitative detection of nitrogen fixation in microbes. The data also demonstrate that GlnLux is sensitive and suggests that the technology may be used for strain improvement (e.g. reducing impact of environmental factors such as nitrogen fertilizer, etc.).

Although a preferred embodiment of the present invention has been described in detail herein with reference to embodiment shown in the examples and illustrated in the accompanying drawings, it is to be understood that the invention is not limited to this embodiment and that various changes and modifications could be made without departing from the scope and spirit of the present invention.

All publications, patents and patent applications referred to above are herein incorporated by reference in their entirety to the same extent as if each individual publication, patent or patent application was specifically and individually indicated to be incorporated herein by reference in its entirety.

REFERENCES

1. Allan, W. L., and B. J. Shelp. 2006. Fluctuations of gamma-aminobutyrate, gamma-hydroxybutyrate, and related amino acids in *Arabidopsis* leaves as a function of the light-dark cycle, leaf age, and N stress. Canadian Journal of Botany 84:1339-1346.
2. Baba, T., T. Ara, M. Hasegawa, Y. Takai, Y. Okumura, M. Baba, K. A. Datsenko, M. Tomita, B. L. Wanner, and H. Mori. 2006. Construction of *Escherichia coli* K-12 in-frame, single-gene knockout mutants: the Keio collection. Molecular Systems Biology 2:0008
3. Bauer, A., K. W. Joy, and A. A. Urquhart. 1977. Amino-acid metabolism of pea leaves—labeling studies on utilization of amides. Plant Physiology 59:920-924.
4. Bredemeier, C., and U. Schmidhalter. 2002. Laser-induced chlorophyll fluorescence to determine the nitrogen status of plants, p. 726-727. In W. J. Horst, M. K. Schenk, J. R. van der Meer, N. Claassen, H. Flessa, W. B. Frommer, H. Goldbach, H. W. Olfs, V. Römheld, B. Sattelmacher, S. Schubert, N. Wirén, and L. Wittenmayer (eds.), Plant Nutrition, vol. 92. Springer Netherlands.
5. Casagrande, M., C. David, M. Valantin-Morison, D. Makowski, and M.-H. Jeuffroy. 2009. Factors limiting the grain protein content of organic winter wheat in southeastern France: a mixed-model approach. Agronomy for Sustainable Development 29:565-574.
6. Chalova, V., C. L. Woodward, and S. C. Ricke. 2006. Application of an *Escherichia coli* green fluorescent protein—based lysine biosensor under nonsterile conditions and autofluorescence background. Letters in Applied Microbiology 42:265-270.
7. Chalova, V. I., W. K. Kim, C. L. Woodward, and S. C. Ricke. 2007. Quantification of total and bioavailable lysine in feed protein sources by a whole-cell green fluorescent protein growth-based *Escherichia coli* biosensor. Applied Microbiology and Biotechnology 76:91-99.
8. Chapman, D. J., and R. M. Leech. 1979. Changes in pool sizes of free amino-acids and amides in leaves and plastids of *Zea mays* during leaf development. Plant Physiology 63:567-572.
9. Chapman, N., and T. Miller. Nitrate transporters and root architecture, p. 165-190. In M. Geisler and K. Venema (ed.), Transporters and Pumps in Plant Signaling. Springer-Verlag Berlin.
10. Chinnusamy, V., B. Stevenson, B.-h. Lee, and J.-K. Zhu. 2002. Screening for gene regulation mutants by bioluminescence imaging. Science STKE 2002:pl10.
11. Christenson, M. A. 2002. Detection systems optimized for low-light chemiluminescence imaging. In K. Van Dyke, C. Van Dyke, and K. Woodfork (ed.), Luminescence Biotechnology: Instruments and Applications. CRC Press, Boca Raton, Fla.
12. Crawford, N. M. 1995. Nitrate—nutrient and signal for plant-growth. Plant Cell 7:859-868.
13. Crawford, N. M., and A. D. M. Glass. 1998. Molecular and physiological aspects of nitrate uptake in plants. Trends in Plant Science 3:389-395.
14. Crochet, A. P., M. M. Kabir, M. B. Francis, and C. D. Paavola. 2010. Site-selective dual modification of periplasmic binding proteins for sensing applications. Biosensors & Bioelectronics 26:55-61.
15. Dattelbaum, J. D., and J. R. Lakowicz. 2001. Optical determination of glutamine using a genetically engineered protein. Analytical Biochemistry 291:89-95.
16. Kahindi, J., N. Karanja, et al. "Biological nitrogen fixation." Biotechnology XV: 104-111.
17. Eckstein, J. A., G. M. Ammerman, J. M. Reveles, and B. L. Ackermann. 2008. Analysis of glutamine, glutamate, pyroglutamate, and GABA in cerebrospinal fluid using ion pairing HPLC with positive electrospray LC/MS/MS. Journal of Neuroscience Methods 171:190-196.
18. Erickson, A. M., I. B. Z. Diaz, Y. M. Kwon, and S. C. Ricke. 2000. A bioluminescent *Escherichia coli* auxotroph for use in an in vitro lysine availability assay. Journal of Microbiological Methods 40:207-212.
19. Susan, H. (1988). "How is nitrogenase regulated by oxygen?" FEMS Microbiology Letters 54(2): 111-129.
20. Fischer, W.-N., B. André, D. Rentsch, S. Krolkiewicz, M. Tegeder, K. Breitkreuz, and W. B. Frommer. 1998. Amino acid transport in plants. Trends in Plant Science 3:188-195.
21. Fonteh, A. N., R. J. Harrington, and M. G. Harrington. 2007. Quantification of free amino acids and dipeptides using isotope dilution liquid chromatography and electrospray ionization tandem mass spectrometry. Amino Acids 32:203-212.
22. Foyer, C. H., M. Parry, and G. Noctor. 2003. Markers and signals associated with nitrogen assimilation in higher plants. Journal of Experimental Botany 54:585-593.
23. Fuentes, S. I., D. J. Allen, A. Ortiz-Lopez, and G. Hernandez. 2001. Over-expression of cytosolic glutamine synthetase increases photosynthesis and growth at low nitrogen concentrations. Journal of Experimental Botany 52:1071-1081.
24. Gholizadeh, A., M. S. M. Amin, A. R. Anuar, and W. Aimrun. 2009. Evaluation of leaf total nitrogen content for nitrogen management in a malaysian paddy field by using soil plant analysis development chlorophyll meter. American Journal of Agricultural and Biological Sciences 4:278-282.
25. Glass, A. D. M., D. T. Britto, B. N. Kaiser, J. R. Kinghorn, H. J. Kronzucker, A. Kumar, M. Okamoto, S. Rawat, M. Y. Siddiqi, S. E. Unkles, and J. J. Vidmar. 2002. The regulation of nitrate and ammonium transport systems in plants. Journal of Experimental Botany 53:855-864.
26. Hitchins, A. D., F. E. McDonough, and P. A. Wells. 1989. The use of *Escherichia coli* mutants to measure the bioavailability of essential amino acids in foods. Plant Foods for Human Nutrition 39:109-120.
27. Jaeger, C. H., S. E. Lindow, S. Miller, E. Clark, and M. K. Firestone. 1999. Mapping of sugar and amino acid availability in soil around roots with bacterial sensors of sucrose and tryptophan. Applied and Environmental Microbiology 65:2685-2690.
28. Kirkman, M. A., and B. J. Miflin. 1979. Nitrate content and amino acid composition of the xylem fluid of spring wheat throughout the growing season Journal of the Science of Food and Agriculture 30:653-660.
29. Lee, R. B., J. V. Purves, R. G. Ratcliffe, and L. R. Sakar. 1992. Nitrogen assimilation and the control of ammonium and nitrate absorption by maize roots. Journal of Experimental Botany 43:1385-1396.
30. Li, P. H., L. Ponnala, N. Gandotra, L. Wang, Y. Q. Si, S. L. Tausta, T. H. Kebrom, N. Provart, R. Patel, C. R. Myers, E. J. Reidel, R. Turgeon, P. Liu, Q. Sun, T. Nelson, and T. P. Brutnell. The developmental dynamics of the maize leaf transcriptome. Nature Genetics 42:1060-U51.
31. Lohaus, G., M. Buker, M. Hussmann, C. Soave, and H. W. Heldt. 1998. Transport of amino acids with special emphasis on the synthesis and transport of asparagine in the Illinois low protein and Illinois high protein strains of maize. Planta 205:181-188.
32. Looger, L. L., M. A. Dwyer, J. J. Smith, and H. W. Hellinga. 2003. Computational design of receptor and sensor proteins with novel functions. Nature 423:185-190.
33. Loper, J. E., and S. E. Lindow. 1994. A biological sensor for iron available to bacteria in their habitats on plant surfaces. Applied and Environmental Microbiology 60:1934-1941.
34. Magalhães, J. R., G. C. Ju, P. J. Rich, and D. Rhodes. 1990. Kinetics of $^{15}NH_4^+$ assimilation in *Zea mays*—preliminary studies with a glutamate dehydrogenase (GDH1) null mutant. Plant Physiology 94:647-656.
35. Majeran, W., G. Friso, L. Ponnala, B. Connolly, M. Huang, E. Reidel, C. Zhang, Y. Asakura, N. H. Bhuiyan, Q. Sun, R. Turgeon, and K. J. van Wijk. 2010. Structural and metabolic transitions of C4 leaf development and differentiation defined by microscopy and quantitative proteomics in maize. The Plant Cell 22: 3509-3042.
36. Mayer, E. P., 0. H. Smith, W. W. Fredricks, and M. A. McKinney. 1975. Isolation and characterization of glutamine-requiring strains of *Escherichia-coli*-K12. Molecular & General Genetics 137:131-142.
37. Meighen, E. A., and R. B. Szittner. 1992. Multiple repetitive elements and organization of the lux operons of luminescent terrestrial bacteria. Journal of Bacteriology 174: 5371-5381.
38. Micallef, B. J., B. J. Shelp, and R. O. Ball. 1989. Quantification of C-14-labeled amino-acids by reverse-phase high-performance liquid-chromatography. Journal of Liquid Chromatography 12:1281-1300.
39. Miflin, B. J., and D. Z. Habash. 2002. The role of glutamine synthetase and glutamate dehydrogenase in nitrogen assimilation and possibilities for improvement in the nitrogen utilization of crops. Journal of Experimental Botany 53:979-987.
40. Miller, A. J., X. R. Fan, Q. R. Shen, and S. J. Smith. 2008. Amino acids and nitrate as signals for the regulation of nitrogen acquisition. Journal of Experimental Botany 59:111-119.
41. Miller, A. J., and S. J. Smith. 1996. Nitrate transport and compartmentation in cereal root cells. Journal of Experimental Botany 47:843-854.
42. Dixon, R. and D. Kahn (2004). "Genetic regulation of biological nitrogen fixation." Nat Rev Micro 2(8): 621-631.
43. Molnár-Perl, I. 2003. Quantitation of amino acids and amines in the same matrix by high-performance liquid chromatography, either simultaneously or separately. Journal of Chromatography A 987:291-309.
44. Montemurro, F., G. Convertini, and D. Fern. 2007. Nitrogen application in winter wheat grown in mediterranean conditions: effects on nitrogen uptake, utilization efficiency, and soil nitrogen deficit. Journal of Plant Nutrition 30:1681-1703.
45. Niu, J. F., F. J. Chen, G. H. Mi, C. J. Li, and F. S. Zhang. 2007. Transpiration, and nitrogen uptake and flow in two maize (Zea mays L.) inbred lines as affected by nitrogen supply. Annals of Botany 99:153-160.
46. Ohlson, M., A. Nordin, and T. Nasholm. 1995. Accumulation of amino acids in forest plants in relation to ecological amplitude and nitrogen supply. Functional Ecology 9:596-605.
47. Oliveira, I. C., and G. M. Coruzzi. 1999. Carbon and amino acids reciprocally modulate the expression of glutamine synthetase in Arabidopsis. Plant Physiol. 121: 301-310.
48. Payne, J. W., G. Bell, and C. F. Higgins. 1977. Use of an Escherichia coli lys-auxotroph to assay nutritionally available lysine in biological materials. Journal of Applied Bacteriology 42:165-177.
49. Peoples, M., and R. Gifford. 1990. Long-distance transport of carbon and nitrogen from sources to sinks in higher plants, p. 442-447. In D. T. Dennis and D. H. Turpin (ed.), Plant Physiology, Biochemistry and Molecular Biology. Longman Singapore Publ., Singapore.
50. Pfleger, B. F., D. J. Pitera, J. D. Newman, V. J. J. Martin, and J. D. Keasling. 2007. Microbial sensors for small molecules: development of a mevalonate biosensor. Metabolic Engineering 9:30-38.
51. Rogers, K. R. 2000. Principles of affinity-based biosensors. Molecular Biotechnology 14:109-129.
52. Rozan, P., Y. H. Kuo, and F. Lambein. 2000. Free amino acids present in commercially available seedlings sold for human consumption. a potential hazard for consumers. Journal of Agricultural and Food Chemistry 48:716-723.
53. Rubio-Covarrubias, 0. A., P. H. Brown, S. A. Weinbaum, R. S. Johnson, and R. I. Cabrera. 2009. Evaluating foliar nitrogen compounds as indicators of nitrogen status in Prunus persica trees. Scientia Horticulturae 120:27-33.
54. Shelp, B. J., and M. C. Dasilva. 1990. Distribution and metabolism of xylem-borne ureido and amino compounds in developing soybean shoots. Plant Physiology 94:1505-1511.
55. Smil, V. 2002. Nitrogen and food production: protein for human diets. Ambio 31:126-131.
56. Wolde-meskel, E., Z. Terefework, et al. (2005). "Genetic diversity and phylogeny of rhizobia isolated from agroforestry legume species in southern Ethiopia." International Journal of Systematic and Evolutionary Microbiology 55: 1439-1452.
57. Tecon, R., and J. R. van der Meer. 2008. Bacterial biosensors for measuring availability of environmental pollutants. Sensors 8:4062-4080.
58. Tejera, N., E. Ortega, R. Rodes, and C. Lluch. 2006. Nitrogen compounds in the apoplastic sap of sugarcane stem: some implications in the association with endophytes. Journal of Plant Physiology 163:80-85.
59. Thiele, B., K. Fullner, N. Stein, M. Oldiges, A. J. Kuhn, and D. Hofmann. 2008. Analysis of amino acids without derivatization in barley extracts by LC-MS-MS. Analytical and Bioanalytical Chemistry 391:2663-2672.
60. Tuffnell, J. M., and J. W. Payne. 1985. A colorimetric enzyme assay using Escherichia coli to determine nutritionally available lysine in biological materials. Journal of Applied Bacteriology 58:333-341.
61. Vidmar, J. J., D. Zhuo, M. Y. Siddiqi, J. K. Schjoerring, B. Touraine, and A. D. M. Glass. 2000. Regulation of high-affinity nitrate transporter genes and high-affinity nitrate influx by nitrogen pools in roots of barley. Plant Physiol. 123:307-318.
62. Wang, Z. H., S. X. Li, and S. Malhi. 2008. Effects of fertilization and other agronomic measures on nutritional quality of crops. Journal of the Science of Food and Agriculture 88:7-23.
63. Yang, H. Y., M. Bogner, Y. D. Stierhof, and U. Ludewig. 2010. $H^+$-independent glutamine transport in plant root tips. PLoS One 5:e8917.
64. Becana, M., J. F. Moran, et al. (1995). "Structure and function of leghemoglobins." An. Estac. Exp. Aula Dei (Zaragoza) 21(3): 203-208.
65. Ott, T., J. T. van Dongen, et al. (2005). "Symbiotic leghemoglobins are crucial for nitrogen fixation in legume root nodules but not for general plant growth and development." Current Biology 15(6): 531-535.
66. Catalano, C. M., W. S. Lane, et al. (2004). "Biochemical characterization of symbiosome membrane proteins from Medicago truncatula root nodules." Electrophoresis 25(3): 519-531.
67. White, J., J. Prell, et al. (2007). "Nutrient sharing between symbionts." Plant Physiology 144(2): 604-614.
68. Boddey, R. M., O. C. Oliveira, et al. (1995). "Biological nitrogen fixation associated with sugar cane and rice: Contributions and prospects for improvement." Plant and Soil 174(1): 195-209.
69. Paau, A. S. (1991). "Improvement of Rhizobium inoculants by mutation, genetic engineering and formulation." Biotechnology Advances 9(2): 173-184.
70. Unkovich, M., D. Herridge, et al. (2008). Measuring plant-associated nitrogen fixation in agricultural systems, Australian Centre for International Agricultural Research.
71. Danso, S. K. A. (1995). "Assessment of biological nitrogen fixation." Nutrient Cycling in Agroecosystems 42(1): 33-41.

The invention claimed is:
1. An essentially glutamine-free medium comprising a glutamine biosensor for detecting glutamine in an analyte, wherein the glutamine biosensor is a whole cell E. coli GlnLux glutamine biosensor.
2. The medium of claim 1, wherein the glutamine biosensor comprises a bacterial cell that is a glutamine auxotroph.
3. The medium of claim 2, wherein the bacterial cell is E. coli.

4. The medium of claim 2, wherein glutamine synthetase is down-regulated in the bacterial cell as compared to a wild-type bacterial cell.

5. The medium of claim 2, wherein the bacterial cell comprises a reporter gene that is expressed in the presence of glutamine.

6. The medium of claim 5, wherein the reporter gene is lux.

7. The medium of claim 1, wherein the growth medium is Lysogeny Broth (LB), M9 medium, agar, or combinations thereof, and optionally comprises casamino acids and/or one or more protease inhibitors.

8. The medium of claim 7, wherein the medium comprises casamino acids in an amount of about 0.5% v/v, and protease inhibitors in an amount of about 1% v/v.

9. The medium of 1, wherein the medium is liquid, solid, or semi-solid, and optionally wherein the glutamine biosensor is diluted up to about 1000-fold.

* * * * *